United States Patent
Wu et al.

(10) Patent No.: US 9,750,783 B2
(45) Date of Patent: Sep. 5, 2017

(54) **COMPOSITION CONTAINING A *SPIRANTHES SINENSIS* EXTRACT AND PHARMACEUTICAL APPLICATIONS THEREOF**

(71) Applicant: National Dong Hua University, Shoufeng, Hualien (TW)

(72) Inventors: Maw-Kuen Wu, Shoufeng (TW); Ching-Feng Weng, Shoufeng (TW); Hung-Yuan Shih, Shoufeng (TW); Huei-Wun Sie, Shoufeng (TW)

(73) Assignee: NATIONAL DONG HUA UNIVERSITY, Shoufeng, Hualien (TW)

( * ) Notice: Subject to any disclaimer, the term of this patent is extended or adjusted under 35 U.S.C. 154(b) by 0 days.

(21) Appl. No.: 14/198,932

(22) Filed: Mar. 6, 2014

(65) Prior Publication Data
US 2015/0250843 A1    Sep. 10, 2015

(51) Int. Cl.
*A61K 36/898* (2006.01)
*A61K 9/00* (2006.01)
*A61K 9/08* (2006.01)

(52) U.S. Cl.
CPC .......... *A61K 36/898* (2013.01); *A61K 9/0019* (2013.01); *A61K 9/08* (2013.01); *A61K 2236/00* (2013.01)

(58) Field of Classification Search
None
See application file for complete search history.

(56) References Cited

PUBLICATIONS

"598. Spiranthes sinensis (Pers.) Ames (Orchidaceae)" from Sung et al., Eds. "International Collation of Traditional and Folk Medicine". World Scientific Co. Pte. Ltd: Singapore, 1997. p. 176 bridging 177.*

Lin et al. J. Nat. Prod. vol. 63 (2000) 1608-1610.*
Fu, Yumei, et al. "Curcumin Protects the Rat Liver from CCl4-Caused Injury and Fibrogenesis by Attenuating Oxidative Stress and Suppressing Inflammation," Molecular Pharmacology, 2008, vol. 73, No. 2, pp. 399-409.
Li, Cong-Ying, et al. "New dimeric phenanthrene and flavone from Spiranthes sinensis," Journal of Asian Natural Products Research, 2013, vol. 15, No. 4, pp. 417-421.
Lin, Yun-Lian, et al. "Dihydrophenanthrenes from Spiranthes sinensis," Journal of Natural Products, 2000, vol. 63, No. 12, pp. 1608-1610.
Lin, Yun-Lian, et al. "Homocyclotirucallane and Two Dihydrophenanthrenes from Spiranthes sinensis," Chemical and Pharmaceutical Bulletin, 2001, vol. 49, No. 9, pp. 1098-1101.
Nakerakanti, Sashidhar, et al. "The Role of TGF-beta Receptors in Fibrosis," The Open Rheumatology Journal, 2012, vol. 6, pp. 156-162.
Peng, Jin-Yong, et al. "Two new prenylated coumarins from Spiranthes sinensis (Pers.) Ames," Journal of Asian Natural Products Research, Mar. 2008, vol. 10, No. 3, pp. 256-259.
Sun, Mei, "Effects of Population Size, Mating System, and Evolutionary Origin on Genetic Diversity in Spiranthes sinensis and S. hongkongensis," Conservation Biology, Jun. 1996, vol. 10, No. 3, pp. 785-795.
Uetake, Yukari, et al. "Changes in actin filament arrays in protocorm cells of the orchid species, Spiranthes sinensis, induced by the symbiotic fungus Ceratobasidium cornigerum," Canadian Journal of Botany, 1997, vol. 75, No. 10, pp. 1661-1669.
Zheng, Shizhong, et al. "Activation of PPARgamma is required for curcumin to induce apoptosis and to inhibit the expression of extracellular matrix genes in hepatic stellate cells in vitro," Biochemical Journal, 2004, vol. 384, pp. 149-157.

* cited by examiner

*Primary Examiner* — Amy L Clark
(74) *Attorney, Agent, or Firm* — Birch, Stewart, Kolasch & Birch, LLP

(57) ABSTRACT

The present invention is related to a pharmaceutical composition comprising an effective amount of a *Spiranthes sinensis* extract and a pharmaceutically acceptable carrier. The present invention improves the economic value of *Spiranthes sinensis* by verifying the efficacies of said pharmaceutical composition in anti-inflammation, anti-liver fibrosis and/or anti-oxidation.

8 Claims, 18 Drawing Sheets

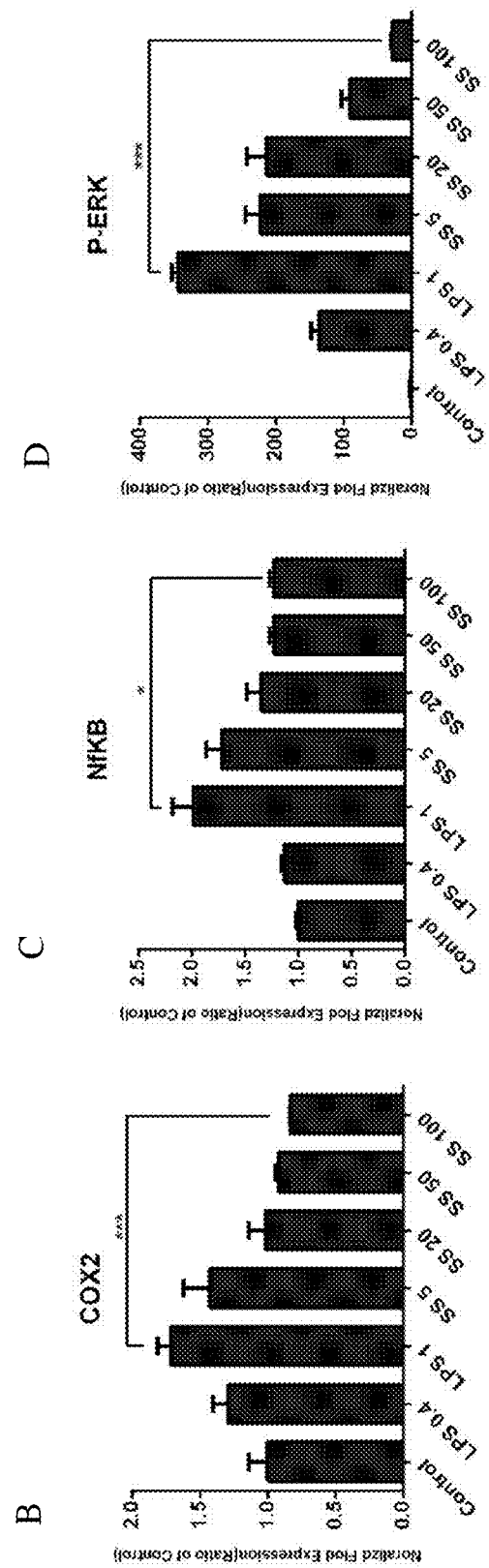
Figure 4 (con.)

A

B

A

B

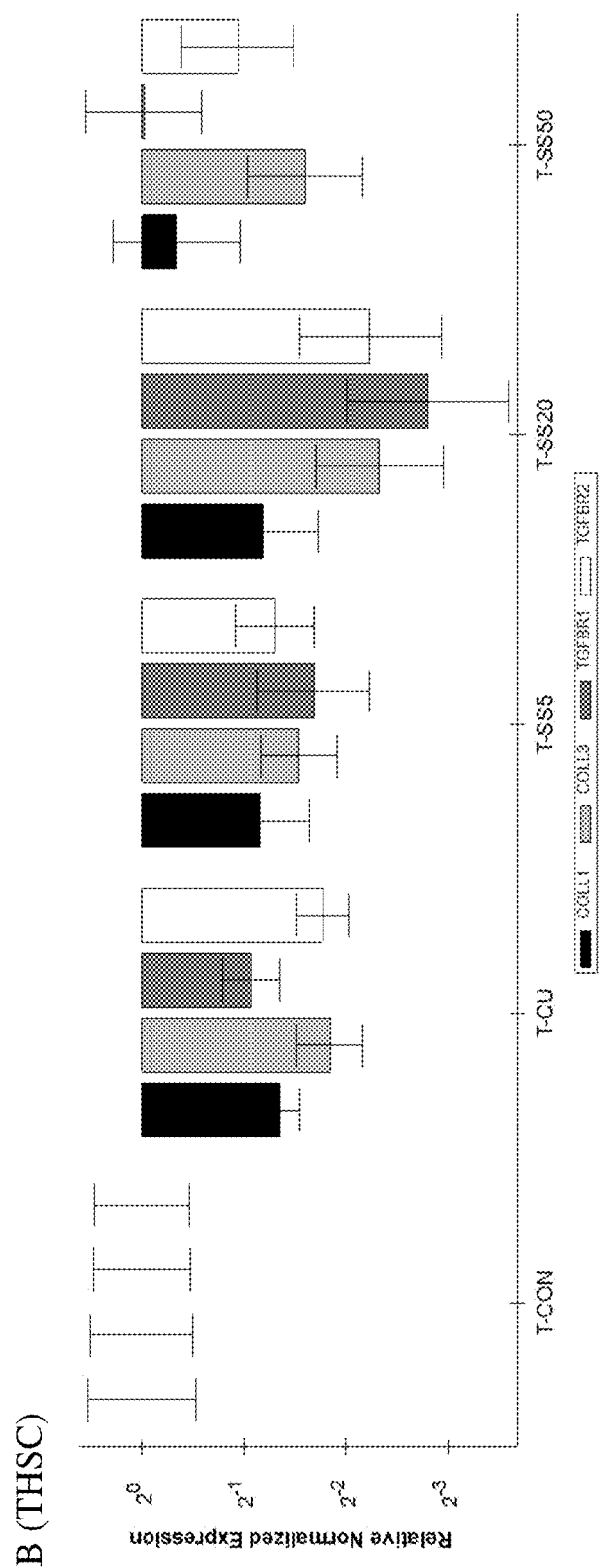
Figure 15 (con.)

COMPOSITION CONTAINING A *SPIRANTHES SINENSIS* EXTRACT AND PHARMACEUTICAL APPLICATIONS THEREOF

BACKGROUND

Technical Field

The present disclosure relates to a method and a pharmaceutical composition for inflammation and/or liver fibrosis treatment; more specifically, to a method and a pharmaceutical composition for inflammation and/or liver fibrosis treatment by using a *Spiranthes sinensis* extract.

Description of Related Art

*Spiranthes sinensis*, commonly known as the Chinese *Spiranthes*, is a species of orchid occurring in much of eastern Asia, west to the Himalayas, south and east to New Zealand, and north to Siberia. Previous phytochemical investigations of *Spiranthes sinensis* showed the presence of dihydrophenanthrenes, sterols, homocyclotirucallane (Lin, Huang et al. 2000, Lin, Wang et al. 2001), two new prenylated coumarins (Peng, Han et al. 2008) and one novel dimeric phenanthrene and flavone (Li, Liu et al. 2013). However, the medicinal properties of *Spiranthes sinensis* crude extract and its phytochemicals is still unexplored yet.

Inflammation is recognized as an onset of immune response for infections or disorders of a subject. However, it is also noted that inflammation may also be harmful to a subject if it is out of control, for example, in an allergy response. Moreover, overly (exuberant) wound healing usually happens from the recovery of severe and out-of-control inflammation, which may result in fibrosis in tissues and then lead to carcinogenesis. Case in point, liver fibrosis occurs during inflammation of liver tissue and is recognized to be involved in cirrhosis and liver cancer. Although inflammation is parts of the defense mechanism of immune system, it is important to appropriately reduce the degree of inflammation in necessary.

Liver fibrosis is scarring process, on behalf of the liver damage response. Liver fibrosis is overly (exuberant) wound healing in which excessive connective tissue builds up in the liver. The extracellular matrix (ECM) is overproduced, degraded deficiently, or both. Over time this process can lead to the cirrhosis of liver, once the development of cirrhosis and severe complications might occur including portal hypertension, liver failure, and liver cancer.

In light of the foregoing, as *Spiranthes sinensis* is expected to have potentials in pharmaceutical applications, further researches of *Spiranthes sinensis* in applications of treating inflammation and/or liver fibrosis are required for improving the economic value of *Spiranthes sinensis*.

SUMMARY

One of the objectives of the present invention is to provide a pharmaceutical composition having efficacies in anti-inflammation, anti-liver fibrosis and/or anti-oxidation; therefore provide novel options for medication.

Another objective of the present invention is to improve the economic value of *Spiranthes sinensis* by verifying novel pharmaceutical applications thereof.

In order to achieve the above-mentioned objects, the present invention provides a pharmaceutical composition having efficacies in anti-inflammation, anti-liver fibrosis and/or anti-oxidation, comprising an effective amount of a *Spiranthes sinensis* extract and a pharmaceutically acceptable carrier; wherein said effective amount is 0.6 to 5 mg/60 kg body weight/day.

Preferably, said pharmaceutical composition comprises 5 to 100 μg/mL of said *Spiranthes sinensis* extract based on the total volume of said pharmaceutical composition.

Preferably, said anti-inflammation comprises down-regulation of inflammatory cytokines, iNOS, Cox-2, NFκB and/or the phosphorylation of ERK.

Preferably, said anti-liver fibrosis comprises accumulating lipid in hepatic stellate cells, down-regulating the proliferation of hepatic stellate cells, inhibiting the mobility of hepatic stellate cells, preventing the activation of hepatic stellate cells, decreasing the synthesis of ECM proteins, or a combination thereof.

Preferably, an administration route of said pharmaceutical composition is via oral administration, intravenous injection, or a combination thereof.

Preferably, said pharmaceutically acceptable carrier is water, alcohol, glycerol, chitosan, alginate, chondroitin, Vitamin E, mineral oil, dimethyl sulfoxide (DMSO), or a combination thereof.

The present invention also provides a method for anti-inflammation, anti-liver fibrosis and/or anti-oxidation, comprising: administrating an effective amount of a *Spiranthes sinensis* extract to a subject; wherein said effective amount is 0.6 to 5 mg/60 kg body weight/day.

Preferably, said administrating is via oral administration, intravenous injection, or a combination thereof.

Preferably, said *Spiranthes sinensis* extract is administrated with a pharmaceutically acceptable carrier; wherein said pharmaceutically acceptable carrier is water, alcohol, glycerol, chitosan, alginate, chondroitin, Vitamin E, mineral oil, dimethyl sulfoxide (DMSO), or a combination thereof.

Preferably, said *Spiranthes sinensis* extract is prepared by the following steps: obtaining a plant of *Spiranthes sinensis*; mixing said plant with a solvent to obtain a mixture; and drying said mixture to obtain said extract.

Preferably, said plant is dried and/or ground before mixing with said solvent.

Preferably, said solvent is ethyl acetate, acetone, n-hexane, or a combination thereof.

Preferably, said ethyl acetate is at a concentration of 5% to 100% (v/v); wherein said concentration is based on the total volume of said ethyl acetate; more preferably, is 10% to 100% (v/v).

Preferably, said mixing is conducted at 20 to 28° C. Preferably, said mixing is conducted for 1 to 2 days. Preferably, said drying is achieved by vacuum drying, freeze-dried, lyphilization, or a combination thereof.

In light of the foregoing, the present invention discloses the novel pharmaceutical applications of *Spiranthes sinensis* in anti-inflammation, anti-liver fibrosis and anti-oxidation. Therefore the economic value of *Spiranthes sinensis* can be improved.

DETAILED DESCRIPTION

Figure 1:
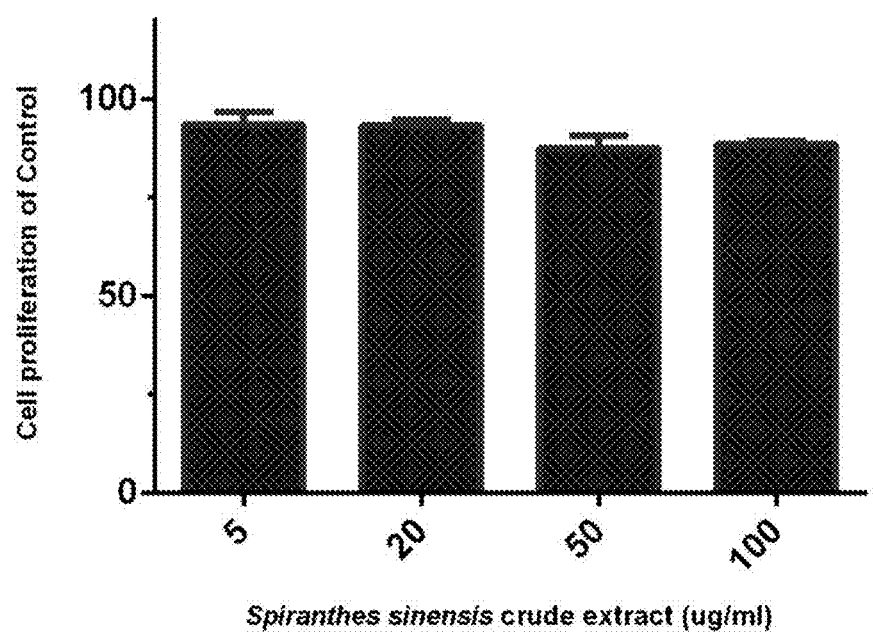
FIG. 1 shows the cell viability experiments for RAW264.7 in Example 2 by using MTT assay. The cells were treated with the present *Spiranthes sinensis* extract at various concentrations of 5, 20, 50, and 100 μg/mL for 24 h. The concentration is based on the volume of the culture medium.

The present invention provides the pharmaceutical applications of *Spiranthes sinensis* by showing its efficacies in anti-inflammation, anti-liver fibrosis, and/or anti-oxidation.

The term "anti-" used herein is referred to as the prevention and/or treatment of a disorder, an illness and/or a disease. The term of "prevention" or "preventing" herein is referred to avoid a subject from the occurrence of a disorder, an illness and/or a disease. The term of "treatment" or "treating" herein is referred to eliminate, stop, or reduce the progress/degree of a disorder, an illness and/or a disease.

The term "anti-inflammation" used herein is referred to as the prevention and/or treatment of an inflammation reaction in a subject. Said anti-inflammation comprises down-regulation of inflammatory cytokines, iNOS, COX-2, NFκB and/or the phosphorylation of ERK. The term of "anti-liver fibrosis" herein is referred to as the prevention and/or treatment of a liver fibrosis in a subject. Said anti-liver fibrosis comprises accumulating lipid in hepatic stellate cells, down-regulating the proliferation of hepatic stellate cells, inhibiting the mobility of hepatic stellate cells, preventing the activation of hepatic stellate cells, decreasing the synthesis of ECM proteins, or a combination thereof. The term of "anti-oxidation" or "anti-oxidant activity" herein is referred to the ability of scavenging, capturing, and neutralizing free radicals.

The term "effective amount" used is herein referred to an amount that is sufficient to perform the aforesaid efficacies (anti-inflammation, anti-liver fibrosis, and/or anti-oxidation). The effective amount obtained in the following animal model (mice) is 0.06 to 0.5 mg/kg body weight/day and the dosage can be calculated as 0.6 to 5 mg/60 kg body weight/day for human.

In one aspect of the present invention, an extract of *Spiranthes sinensis* is provided; more specifically said extract is an ester extract. Said ester extract is prepared at least by the following steps: obtaining a plant of *Spiranthes sinensis*; mixing said plant with a solvent to obtain a liquid; and drying said liquid to obtain said ester extract of *Spiranthes sinensis*.

Said plant of *Spiranthes sinensis* may be any parts of *Spiranthes sinensis* including but not limit to: a root, a stem, a leaf or a whole plant thereof. Preferably, said plant of *Spiranthes sinensis* is dried before being proceeded to the following steps. More preferably, said plant of *Spiranthes sinensis* is dried and ground into proper size so that the interaction between said plant and said solvent can be more effective.

Said solvent is ethyl acetate, acetone, n-hexane, or a combination thereof. Preferably, said solvent is ethyl acetate. In a preferable embodiment of the present invention, an ethyl acetate of a concentration of 5 to 100% (v/v) is used; wherein said concentration is based on the total volume of said ethyl acetate; more preferably, is 10% to 100% (v/v).

Said mixing is conducted at 20 to 28° C. Preferably, said mixing is conducted for 1 to 2 days. Alternatively, said mixing can be performed by immersing said plant into said solvent.

Said drying can be achieved by vacuum drying, freeze-dried, lyophilization or a combination thereof. In an alternative embodiment, said extract is in the form of powder after said drying.

In another aspect of the present invention, a pharmaceutical composition is provided, which comprises 5 to 100 µg/mL of said *Spiranthes sinensis* extract based on the total volume of said pharmaceutical composition. Said pharmaceutical composition has an effective amount of 0.6 to 5 mg/60 kg body weight/day for providing efficacies in anti-inflammation, the anti-liver fibrosis, and/or anti-oxidation.

In yet another aspect of the present invention, a method for anti-inflammation, anti-liver fibrosis and/or anti-oxidation, is provided. The method comprises administrating an effective amount of the ester extract to a subject. Preferably, said ester extract is administrated to said subject in the form of said pharmaceutical composition while the effective amount of the ester extract is 0.6 to 5 mg/60 kg body weight/day.

In a preferable embodiment of the present invention, the route of said administrating is via oral administration, intravenous injection, or a combination thereof.

In a preferable embodiment of the present invention, said pharmaceutically acceptable carrier is water, alcohol, glycerol, chitosan, alginate, chondroitin, Vitamin E, mineral oil, dimethyl sulfoxide (DMSO), or a combination thereof.

The following embodiments recite the research of the present invention. In order to clearly describe the present invention, the researches of the present invention are divided into three parts. The first part was made by an in vitro RAW 264.7 macrophage cell culture system, including the examination in NO content, pro-inflammatory cytokines, nitric oxide synthesis, and anti-oxidation. The second part was performed in a mice model including examining the anti-inflammation activity and the effect on MMP 9 activity in vivo. The last part of the research was made by in vitro THSCs and NHSCs culture system, including examination in fatty acid storage, collagen synthesis, MMP activity, expression of fibrosis-related genes.

The following embodiments are recited for further explaining the advantages of the present invention but not for limiting the claim scope of the present invention.

Example 1: Preparation of *Spiranthes sinensis* Extract of the Present Invention The dried *Spiranthes sinensis* was obtained from a local market, Hualien, Taiwan, in August, 2013. The dried *Spiranthes sinensis* was ground into powder and extracted with 100% ethyl acetate (preferably, 10 fold dry weight volumes) for one week at room temperature (RT). The liquid extract was in vacuo evaporated to produce its dried powder with a yield of 20.9% on a dry weight basis. For the following experiments, a stock composition was made by dissolving said extract in DMSO at a concentration of 1 mg/mL based on the total volume of said DMSO.

$1^{st}$ Part Example 2-Example 5

RAW 264.7 Macrophage Cell Culture System

Data were expressed as means±SEM. Statistical comparisons of the results were made using one-way analysis of variance (ANOVA). Means within each column followed by the different letters are significantly different at $p<0.05$ by Tukey's test.

Example 2: Cell Culture and Viability

[RAW264.7]

The RAW264.7 murine macrophage cell line, which is commonly used for study of inflammation, was purchased from the Bioresource Collection and Research Center (BCRC, Taiwan). The cells were incubated at 37° C. in 5% $CO_2$ in Dulbecco's modified Eagle's medium (DMEM; Gibco Inc., NY, USA) supplemented with 100 U/mL penicillin, 100 µg/mL sodium pyruvate and 10% fetal bovine serum (FBS; Gibco Inc.).

The cells were also treated with 0.01% DMSO as a vehicle control. The cells were seeded into 12-well plates at a density of $6 \times 10^5$ cells/well in 24 h then incubated with 0.1% BSA with serum-free medium 3 h, treated with various concentrations (5, 10, 20, 50, and 100 µg/mL) of the present *Spiranthes sinensis* extract and then incubated in the presence of LPS (0.4 or 1 µg/mL) for additional 4 h.

[Cell Viability]

In order to examine the bio-compatibility of the extract of the present invention, a MTT assay (3-(4,5-dimethylthiazol-2-yl)-2,5-diphenyltetrazolium bromide (MTT, Invitrogen), a colorimetric based assay) was performed in this example.

Briefly, 8×10³ of cells per well was seeded in 96-well plates and were incubated in 5% $CO_2$ at 37° C. for overnight. Cells were treated different concentrations (5, 20, 50, and 100 μg/mL) of *Spiranthes sinensis* crude extract for 24 h, after incubation 20 μL (5 mg/mL) of MTT solution was added per well and further incubated for 4 h. The media was removed, and formazan was solubilized by adding 100 μL/well of DMSO (Sigma-Aldrich) and OD was measured at 570 nm using a microplate reader (ELISA reader, Thermo Labsystems). Percentage of viable cells was estimated by comparing with untreated control cells. The average absorbance value of the control cells was taken as 100% viability.

The results showed the present extract of *Spiranthes sinensis* substantially has no harm to the cells at given dosages (FIG. 1).

Figure 2:
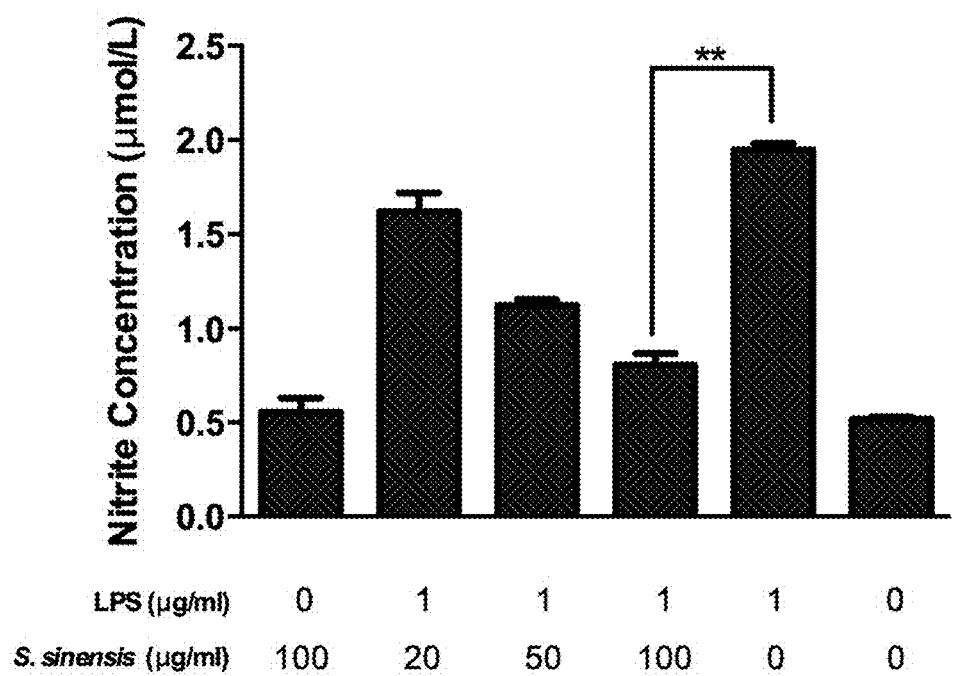
FIG. 2 shows the effect of the present *Spiranthes sinensis* extract on NO release. ** P<0.01 as compared with 10 μg/mL of the present *Spiranthes sinensis* extract group.

Example 3: The Effect of the Present *Spiranthes sinensis* Extract on $NO_2$-Production $NO_2$-production was determined in the cell culture supernatants by the Griess reaction. RAW 264.7 cells were cultured and treated as recited in the above Example 2 and the supernatant was collected. 200 μL/well of the supernatant were placed in a 96 well plate and 20 μL of 6.5 M hydrochloric acid and 20 μL of 37.5 mM sulfanilic acid were added. After incubation for 10 min at room temperature, 20 μL of 12.5 mM N (1-napthyl) ethylendiamine was added. Optical density was read at 550 nm 30 min later and compared with a standard curve. The results (FIG. 2) showed the inhibition effect of the present *Spiranthes sinensis* extract on NO release in a dose-dependent manner.

Example 4: The Effect of the Present *Spiranthes sinensis* Extract on the Expression of iNOS, Pro-Inflammatory Cytokines, COX-2, NFκB and the Phosphorylation and ERK RAW 264.7 cells were cultured and treated as recited in the above example 2. The expressions of iNOs, TNF-Alpha, IL 1, and IL 6 of the cells were examined by Real-time PCR while the expression of Cox-2, NFκB, p-ERK and ERK were examined by Western blot.

[Real-Time PCR]

Total RNA was prepared from freshly harvested RAW 264.7 cells and was isolated using Trizol extraction. RNA samples were frozen at −80° C. until analyzed. cDNA was then made using an M-MLV RT kit (Invitrogen, Carlsbad, Calif.) according to the manufacturer's protocol.

The expression of selected cytokine and related genes in mouse tissue and in RAW264.7 cells exposed to the present *Spiranthes sinensis* extract was determined by the Sensi-FAST SYBR No-ROX Kit (BIOLINE, London, UK), as described previously. PCR cycling conditions for TNF-Alpha included a 95° C. heating step for 2 min at the beginning of every run. The tubes were then cycled at 95° C. for 5 sec, annealed at 60° C. for 10 sec, and extended at 72° C. for 20 sec for forty cycles. PCR conditions for iNOs, IL6, and IL1 included a 95° C. heating step for 2 min at the beginning of every run. The tubes were then cycled at 95° C. for 5 sec, annealed at 64° C. for 10 sec, and extended at 72° C. for 20 sec for thirty-eight cycles. In all cases, optical data were collected during the annealing phase. In order to quantify expression represented by each of the PCR products, an internal reference by β-actin. The primers used in the real-time PCR of this example are listed in the following table 1.

TABLE 1

Primers for Real-time PCR

| Name | Sequences 5'->3' | SEQ ID NO |
|---|---|---|
| β-actin Forward | AGT GGT ACG ACC AGA GGC ATA C | SEQ ID NO 01 |
| β-actin Reverse | ATG GGT CAG AAG GAC TCC TAC G | SEQ ID NO 02 |
| iNOs Forward | TCC TAC ACC ACA CCA AAC | SEQ ID NO 03 |
| iNOs Reverse | CTC CAA TCT CTG CCT ATC C | SEQ ID NO 04 |
| TNF Alpha Forward | AAC CCT CTG GCC CAA GGA | SEQ ID NO 05 |
| TNF Alpha Reverse | GGC GAC GGG CTT ATC TGA | SEQ ID NO 06 |
| Interleukins (IL)-6 Forward | ATG AAC TCC CTC TCC ACA AGC | SEQ ID NO 07 |
| Interleukins (IL)-6 Reverse | TGG CTT TGT CTG GAT TCT TTC | SEQ ID NO 08 |
| Interleukins (IL)-1 Forward | AAA GGG GAC TTG AAG AGA G | SEQ ID NO 09 |
| Interleukins (IL)-1 Reverse | CTG CTT GAG AGG TGC TGA TGT | SEQ ID NO 10 |

[Western Blot]

The concentrations of proteins from whole-cell lysates were determined by Bradford assay. Equal amounts (30 μg) of protein were separated by SDS-PAGE and transferred onto PVDF membranes. The blots were then blocked overnight with 5% (wt/vol) nonfat dry milk, and probed with anti-Cox-2 antibodies, anti-NFκB antibodies, phospho-specific antibodies to ERK and anti-ERK antibodies in 5% (wt/vol) BSA dissolved in TBST [20 mM Tris-HCl buffer, pH 7.6, containing 137 mM NaCl and 0.05% (vol/vol) Tween-20]. With the use of horseradish peroxidase-conjugated secondary anti-rabbit or anti-mouse antibody, bound antibodies were detected by enhanced chemiluminescence.

Figure 3:
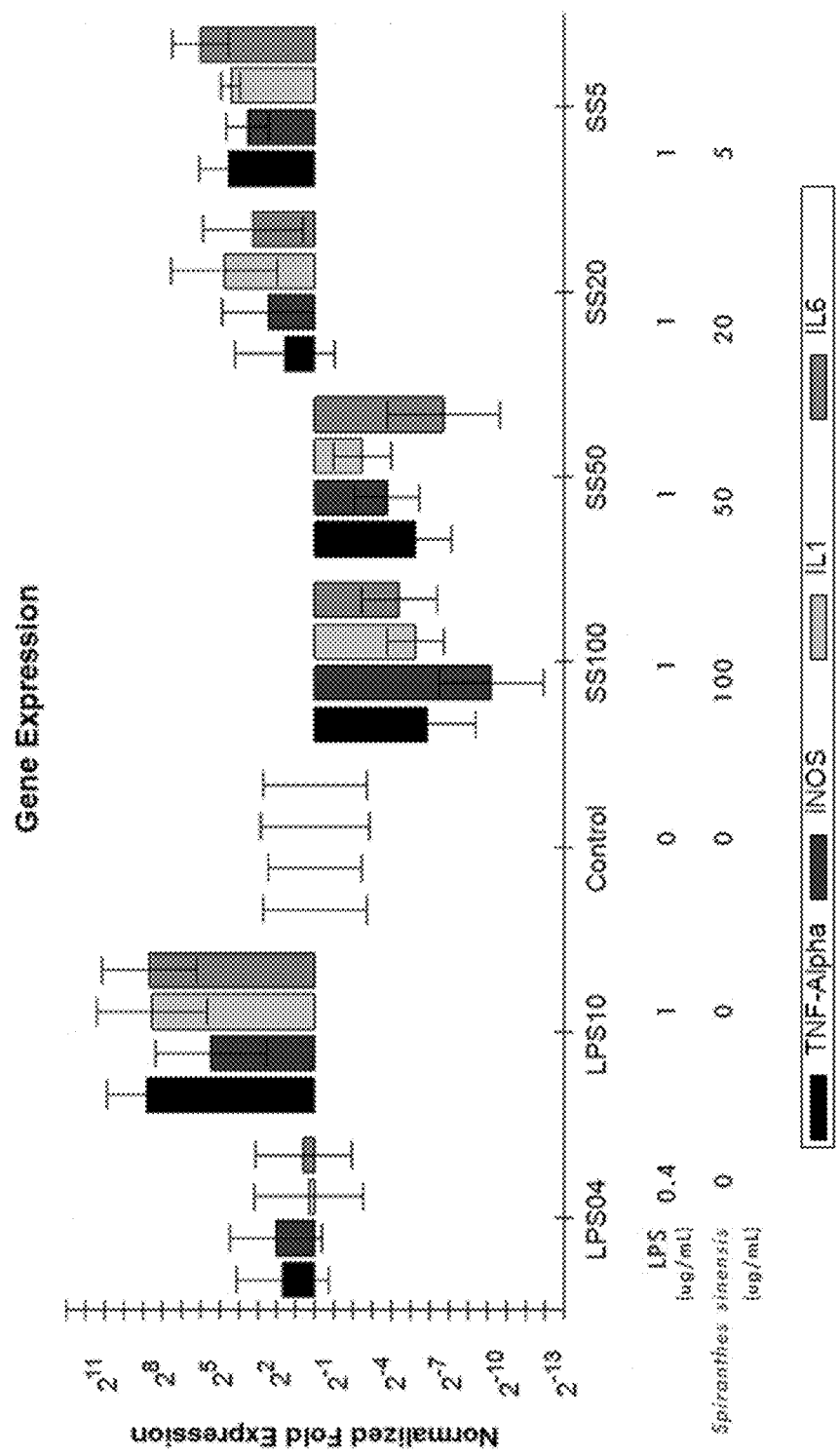
FIG. 3 is the result of Real time PCR showing the expression of TNF-alpha, iNOs, IL-1, and IL-6 mRNA. Data represent the mean±SEM from three separate experiments. LPS04: cells treated with 0.4 µg/mL LPS only; negative control. LPS10: cells treated with 1 µg/mL LPS only; negative control. Control: blank control. SS100: cells treated with 1 µg/mL LPS plus 100 µg/mL of *Spiranthes sinensis* extract. SS50: cells treated with 1 µg/mL LPS plus 50 µg/mL of *Spiranthes sinensis* extract. SS20: cells treated with 1 µg/mL LPS plus 20 µg/mL of *Spiranthes sinensis* extract. SS5: cells treated with 1 µg/mL LPS plus 5 µg/mL of *Spiranthes sinensis* extract. The concentration is based on the volume of the culture medium.
Figure 4:
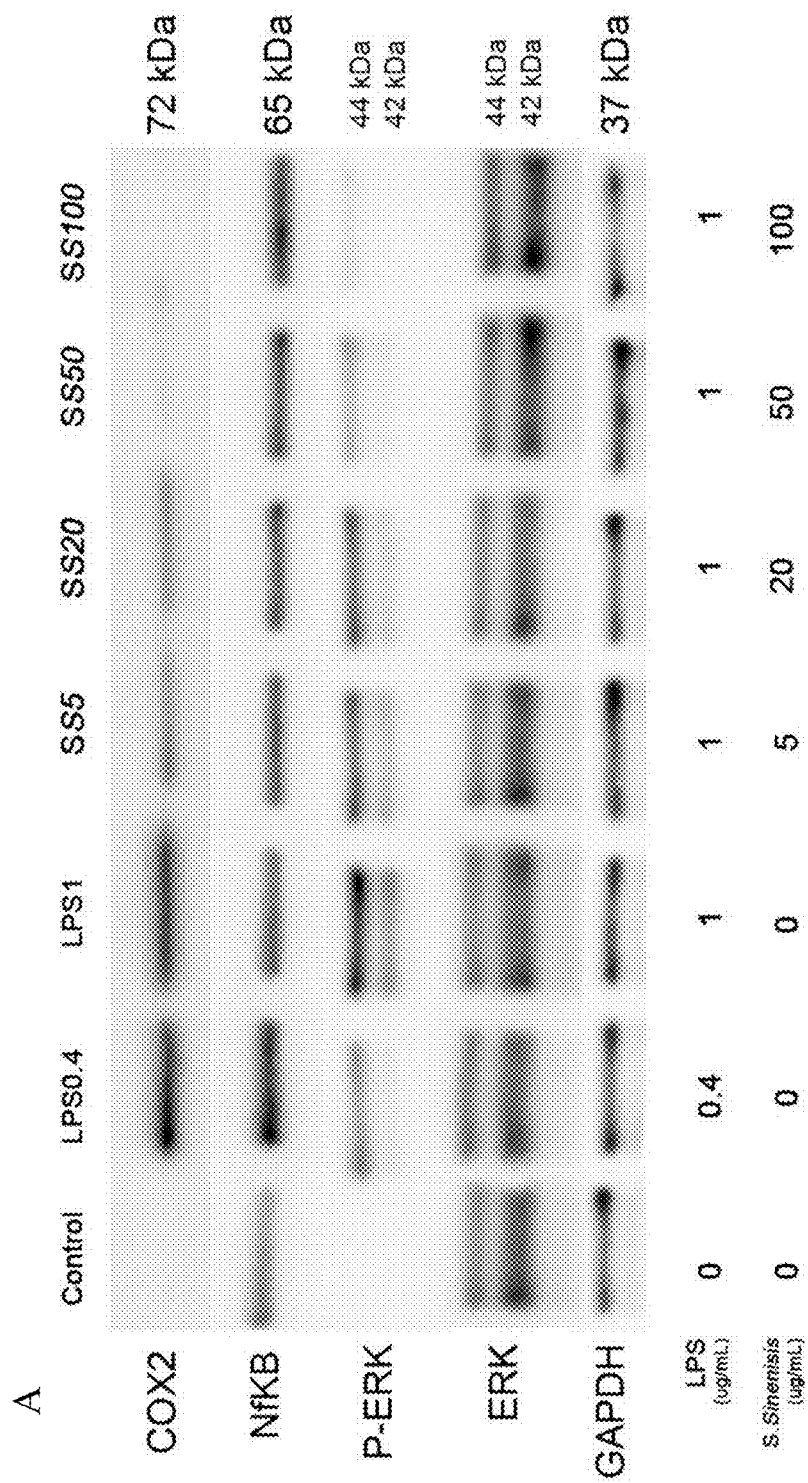
FIG. 4 shows the expression of Cox-2, NFκB, p-ERK, and ERK measured by Western blot. (A) Results of SDS-PAGE. (B), (C), (D) Quantitation of the expression of Cox-2, NFκB, and p-ERK respectively from the results of the Western blot. Control: blank control. LPS04: cells treated with 0.4 µg/mL LPS only; negative control. LPS10: cells treated with 1 µg/mL LPS only; negative control. SS100: cells treated with 1 µg/mL LPS and 100 µg/mL of *Spiranthes sinensis* extract. SS50: cells treated with 1 µg/mL LPS plus 50 µg/mL of *Spiranthes sinensis* extract. SS20: cells treated with 1 µg/mL LPS plus 20 µg/mL of *Spiranthes sinensis* extract. SS5: cells treated with 1 µg/mL of LPS plus 5 µg/mL of *Spiranthes sinensis* extract. The concentration is based on the volume of the culture medium.

According to the results shown in FIGS. 3 and 4, the present *Spiranthes sinensis* extract diminished LPS-induced inflammatory cytokine and iNOS transcription, expression of Cox-2 and NFκB as well as the phosphorylation of ERK in a dose-dependent manner.

Figure 5:
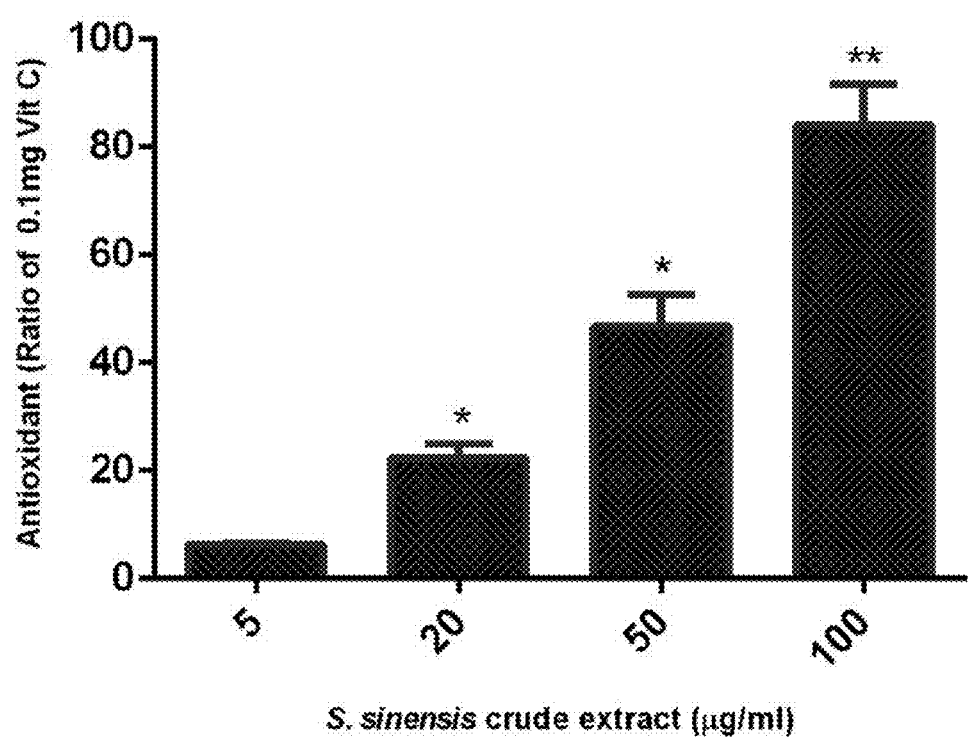
FIG. 5 shows the result of DPPH assay indicating the anti-oxidant activity of the present *Spiranthes sinensis* extract.

Example 5: The Anti-Oxidant Activity of the Present *Spiranthes sinensis* Extract The DPPH radical scavenging activity of *Spiranthes sinensis* was determined as previously described (Sharma and Bhat 2009). In brief, the reaction mixtures containing various concentrations of the present *Spiranthes sinensis* extract and 0.04 mM DPPH in a 96-well microtiter plate were incubated at 37° C. for 30 min, and the absorbance was measured at 490 nm. Vitamin C was used as a positive control. The anti-oxidant activity of the present *Spiranthes sinensis* extract was shown based on the anti-oxidant activity of 0.1 mg of Vitamin C as 100%. The results shown in FIG. 5 indicate that the present *Spiranthes sinensis* extract has comparable ability with Vitamin C in anti-oxidation.

$2^{nd}$ Part Example 6-Example 7

Mice Model

Data were expressed as means±SEM. Statistical comparisons of the results were made using one-way analysis of variance (ANOVA). Means within each column followed by the different letters are significantly different at $p<0.05$ by Tukey's test.

Example 6: The Anti-Inflammatory Activity of the Present *Spiranthes sinensis* Extract

[Animal]

Male C57BL/6 mice were obtained from the National Laboratory Animal Center (Taipei, Taiwan) and kept at controlled environmental conditions with room temperature (22±2° C.), humidity (50±10%). The 12 h light (0600 am-1800 pm) and dark cycle was maintained throughout the study. Animal experiments were approved by the National Dong-Hwa University Animal Ethics Committee and were used according to the "Guide for the Care and Use of Laboratory Animals" of National Dong-Hwa University.

Animals were separated into 6 groups, which are respectively injected with various dosage of the present *Spiranthes sinensis* extract (0.06, 0.3, 0.5 mg/kg body weight), 0.3 mg/kg body weight of trimcinolone (positive control), 3 mg/kg body weight of sevatrim (positive control) and DMSO (negative control). To produce a chronic inflammatory response, mice were then injected with 20 μL of Complete Freund's Adjuvant (*Mycobacterium tuberculosis*; Sigma, St. Louis, Mo., USA) subcutaneously in the plantar surface of the right hind paw (i.pl.). The left hind paw was taken as a control.

The anti-inflammatory effect was examined for 4 days and the swelling index was recorded every day after the injection. The swelling index was calculated by the following formula below and presented as a ratio based on the swelling index before injection (Day 0).

$$\frac{\text{Length} \times \text{Width of right } hindpaw \text{ (injected paw)}}{\text{Length} \times \text{Width of left } hindpaw \text{ (uninjected paw)}}$$

Figure 6:
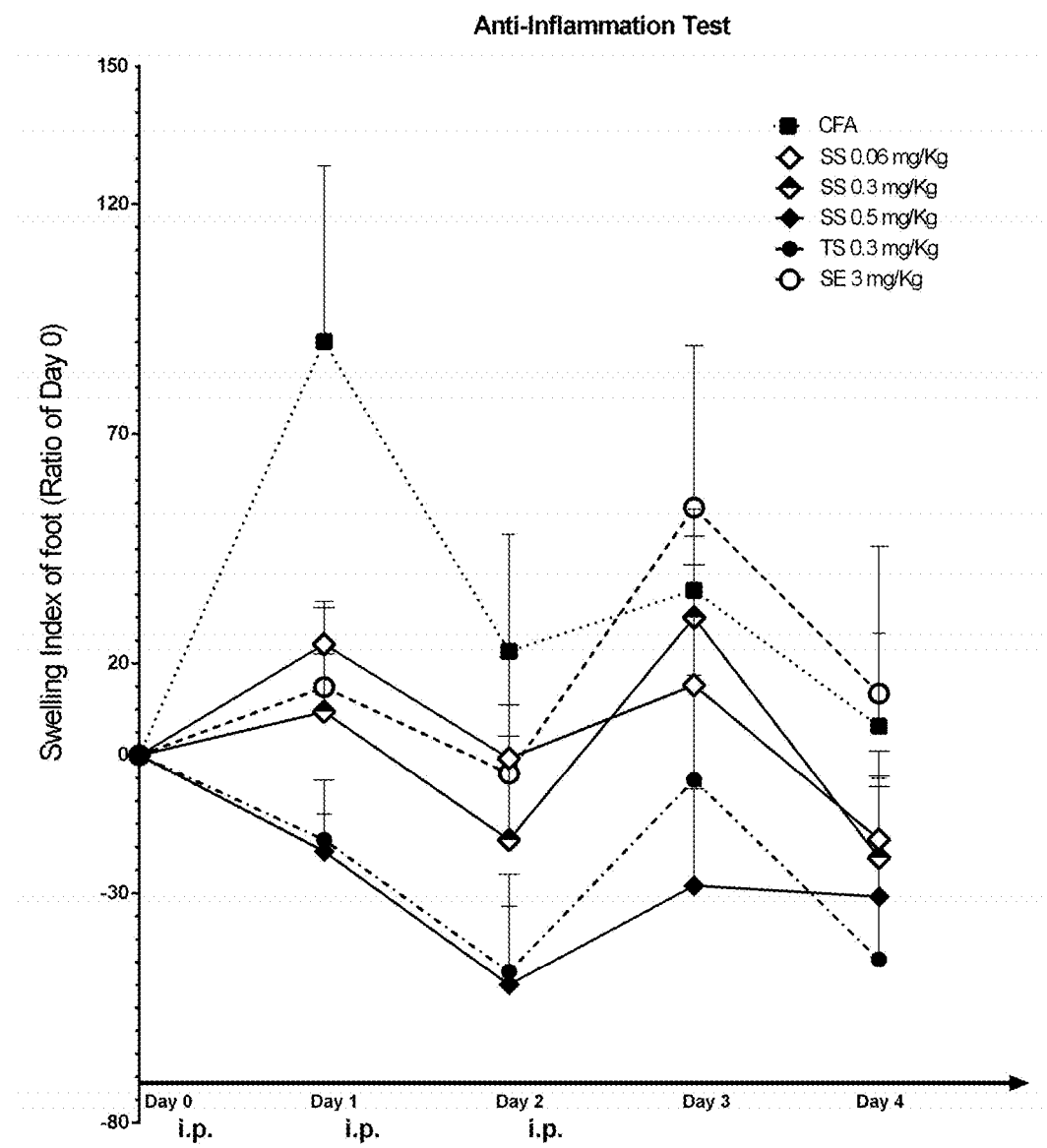
FIG. 6 shows the change in the swelling index of foot. CFA: negative control (injected with Complete Freund's Adjuvant but without treatment). SS: the present *Spiranthes sinensis* extract. TE: triamcinolone. SE: sevatrim. n=5.
Figure 7:
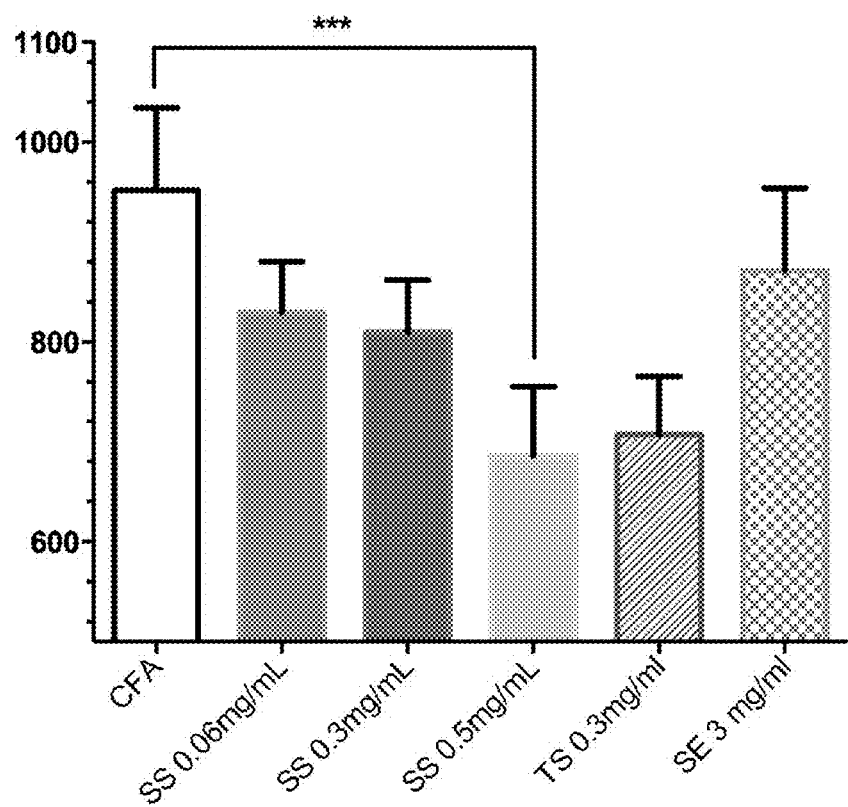
FIG. 7 shows the area under curve calculated from the results shown in FIG. 6. CFA: negative control (induced by CFA but without treatment). SS: the present *Spiranthes sinensis* extract. TE: triamcinolone. SE: sevatrim.

The results were shown in FIG. 6 and the area under curve (AUC) was calculated and presented in the bar diagram of FIG. 7. The results show that by injecting with the present *Spiranthes sinensis* extract, the inflammation (represented by the swelling index) was reduced significantly in a dosage-dependent manner.

Example 7: The Effect of the Present *Spiranthes sinensis* Extract on the Activity of MMP 9

Mice tested in the experiment of example 6 were subjected to further examination for the activity of MMP 9 (matrix metalloproteinase-9). Blood samples were collected from the tail vein at Day 4. The blood were pre-heated at 55° C. with 2× loaded dye (0.125 M Tris-HCl, pH 6.8, 4% SDS, 0.04% Bromophenol blue, 20% Glycerol). 8% SDS-PAGE gels were prepared containing 10% gelatin. 5 μL of blood sample was loaded into gel and electrophoresis separation was performed at 80V for 2-3 h. After electrophoresis, gel was washed 2 times in 50 mL of 2.5% Triton X-100 per gel, and then incubated in developing buffer (0.05 M Tris-HCl, pH 8.8, 5 mM $CaCl_2$, 0.02% $NaN_3$) at 37° C. for 16 h. Finally, gel was stained in 0.1% Coomassie blue R-250 (Bio-Rad) for 4 h and then destained by fixing buffer (45% methanol, 10% acetic acid). Gels were scanned using Epson scanner and quantified using multi-gauge software (Fujifilm). This method has capability to detect the active form and latent form of MMP 9 at their correct molecular weight size.

Figure 8:
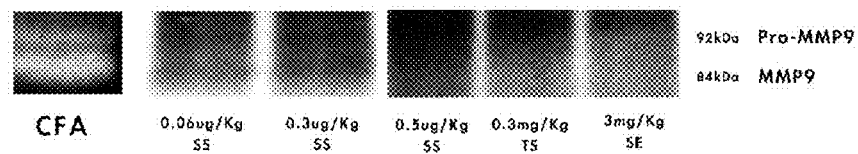
FIG. 8 shows the results of the gelatin zymography for determination of the gelatinolytic activity of MMP 9 in the Example 7. CFA: negative control (induced by CFA but without treatment). SS: the present *Spiranthes sinensis* extract. TE: triamcinolone. SE: sevatrim.

The results in FIG. 8 indicated an inhibitory effect on the activity of MMP 9 by treating with the present *Spiranthes sinensis* extract. MMP 9 is a kind of gelatinase and is recognized to be up-regulated during liver fibrosis. Therefore, the results hinted the present *Spiranthes sinensis* extract's efficacy in treating inflammation.

$3^{rd}$ Part Example 8-Example 12

THSCs and NHSCs Cell Culture System

Data were expressed as means±SEM. Statistical comparisons of the results were made using one-way analysis of variance (ANOVA). Means within each column followed by the different letters are significantly different at $p<0.05$ by Tukey's test.

Example 8: Cell Culture and Viability

[NHSCs and THSCs]

Hepatic Stellate Cells (HSCs), one of non-parenchymal cell, is the major cell type involved in liver fibrosis, which is the formation of scar tissue in response to liver damage. In normal liver, HSCs keep in quiescent form and is principal storage site of vitamin A and lipids. The stored amount of vitamin A decreases progressively in liver injury. When the liver is damaged, stellate cells are changed into an activated state (Hjelkrem, Morales et al. 2012). The activated stellate cell is characterized by proliferation, contractility, and chemotaxis. Therefore, the quiescent form of HSC presents the indication of liver condition.

Non chemical-induced hepatic stellate cells (NHSCs >95% purity) were isolated from male Sprague-Dawley rat liver, and thioacetamide (TAA)-induced hepatic stellate cells (THSCs >95% pure) were isolated from TAA (Fluka) induced fibrotic liver of male Sprague-Dawley rat as our previous study described. Both the cell lines were maintained in DMEM (pH 7.4) supplemented with 10% FBS, and incubated at 37° C. with 5% $CO_2$ in water saturated incubator. Media was changed in every 2 days and the cells were passage during 80%-90% confluence using trypsin/EDTA (Sigma-Aldrich).

[Cell Viability]

In order to examine the bio-compatibility of the extract of the present invention, a MTT assay (3-(4,5-dimethylthiazol- 2-yl)-2,5-diphenyltetrazolium bromide (MTT, Invitrogen), a colorimetric based assay) was performed in this example.

Briefly, $1\times10^4$ of cells per well (for NHSCs and THSCs) was seeded in 96-well plates and were incubated in 5% $CO_2$ at 37° C. for overnight. Cells were treated different concentrations (5, 20, 50, and 100 µg/mL) of *Spiranthes sinensis* crude extract for 24 h, after incubation 20 µL (5 mg/mL) of MTT solution was added per well and further incubated for 4 h. The media was removed, and formazan was solubilized by adding 100 µL/well of DMSO (Sigma-Aldrich) and OD was measured at 570 nm using a microplate reader (ELISA reader, Thermo Labsystems). Percentage of viable cells was estimated by comparing with untreated control cells. The average absorbance value of the control cells was taken as 100% viability.

Figure 9:
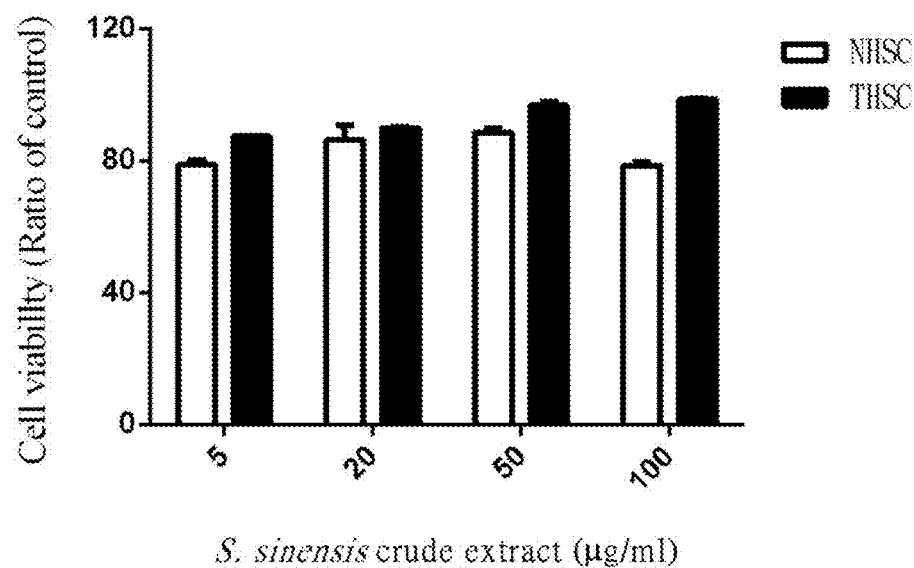
FIG. 9 shows the cell viability experiments for NHSCs and THSCs by using MTT assay. The cells were treated the present *Spiranthes sinensis* extract at various concentrations of 5, 20, 50, and 100 µg/mL for 24 h. The concentration is based on the volume of the culture medium.

The results showed that the present extract of *Spiranthes sinensis* substantially has no harm to the cells at given dosages (FIG. 9).

Example 9: The Effect of the Present *Spiranthes sinensis* Extract in Lipid Accumulation In this example, an Oil red O staining assay and an AdipoRed assay were used for examining the effect of the present *Spiranthes sinensis* extract in Lipid accumulation.
[Oil Red O Staining Assay]

Briefly, $1\times10^5$ of cells per well (NHSCs or THSCs) were seeded in 6-well plates and were incubated in 5% $CO_2$ at 37° C. overnight for confluence. Afterward, cells were treated with various concentrations (5, 20, and 50 µg/mL) of the present *Spiranthes sinensis* extract for 24 h, respectively. Cells were washed twice with PBS, and then fixed by 3.7% paraformaldehyde (pre-warmed) for 10 min. Oil red O stock solution 0.5% (w/v) in isopropanol (Fluka) was diluted with 60% volume of water, filtered, and stained at RT under the dark for 1 h. Cells were washed with 50% isopropanol for 5 sec and counterstained with Hematoxylin (Sigma-Aldrich) for 1 min. Cells were washed with distilled water for three times and stored using glycerol. Images were acquired using ZEISS inverted microscope connected with Canon 700 D camera.

Figure 10:
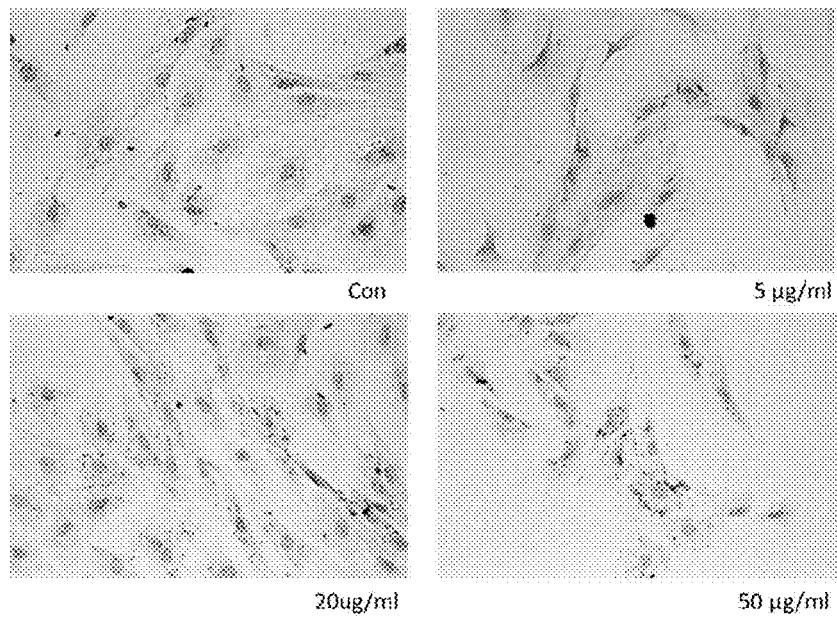
FIG. 10 shows the results of the oil red o staining assay in Example 9 under 240× magnification; wherein (A) NHSCs, untreated, or treated with 5, 20, and 50 µg/mL of *Spiranthes sinensis* extract; (B) THSCs, untreated, or treated with 5, 20, and 50 µg/mL of *Spiranthes sinensis* extract.
Figure 10:
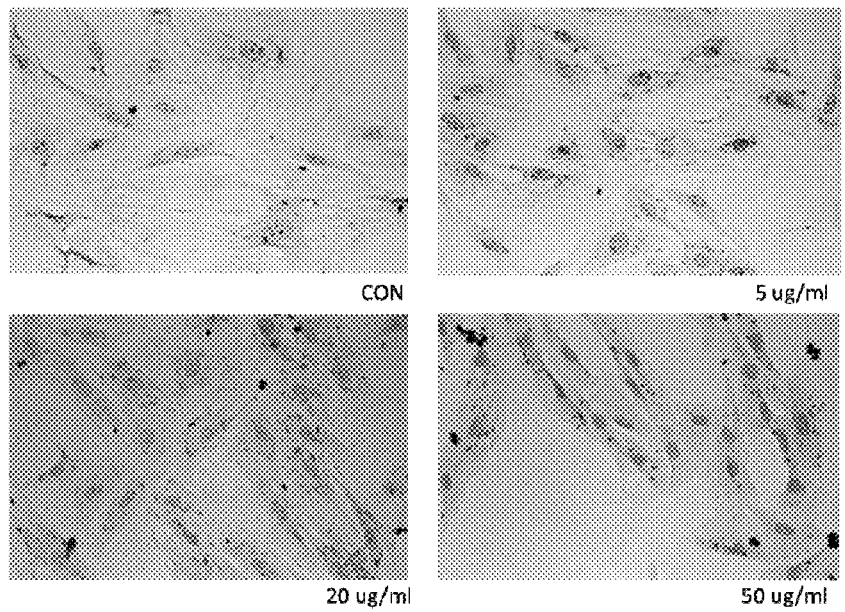
Figure 11:
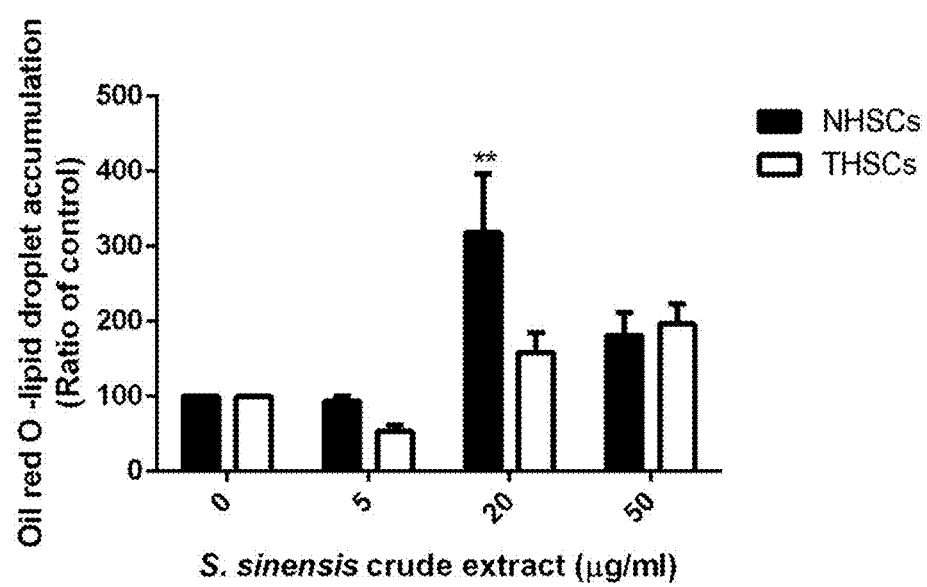
FIG. 11 is a bar diagram showing the quantitation from the results of the experiments shown in FIG. 10.

The results are shown in FIG. 10. It is noted that, the present *Spiranthes sinensis* extract increases the abundant perinuclear lipid droplets both in NHSCs and THSCs when compared with the control group. The results of FIG. 10 are also quantified as the bar chart shown in FIG. 11 from which it is more obvious that the treatment of the present *Spiranthes sinensis* extract respectively increases the fatty acid storage of NHSCs and THSCs in about 3 fold and about 1.5 fold compare with the untreated control groups.
[AdipoRed Assay]

$1\times10^4$ of cells per well were seeded in 96-well plates and incubated in 5% $CO_2$ at 37° C. overnight. Cells were treated with various concentrations (5, 20, 50, and 100 µg/mL) of *Spiranthes sinensis* extract for 48 h. After incubation, the culture supernatant was removed and each well carefully rinsed with 200 µL of PBS. And then, each well was filled with 200 µL of PBS and 5 µL of AdipoRed Reagent (Lonza, Walkersville, Md., USA). After incubation at room temperature for 10 min, placed the plate in the fluorimeter and fluorescence with excitation at 485 nm and emission at 572 nm (Multimode Plate Reader, PerkinElmer Inc Waltham, Mass., USA) was acquired.

Figure 12:
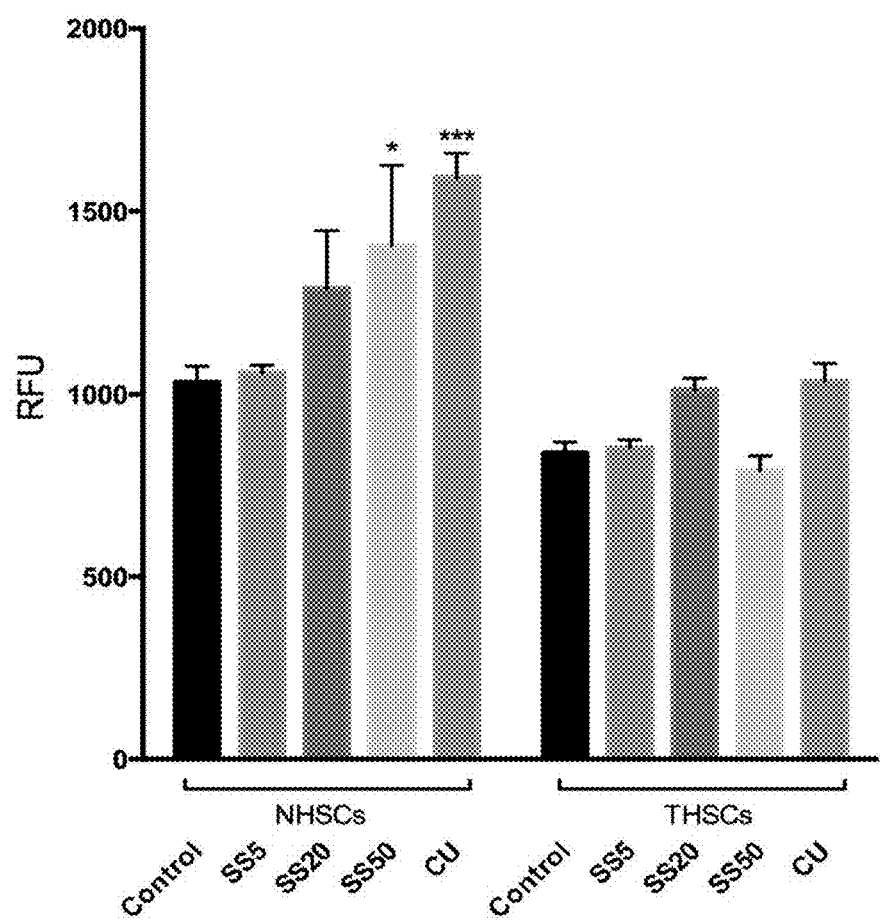
FIG. 12 shows the effect of the present *Spiranthes sinensis* extract (5, 20 and 50 µg/mL) and curcumin (25 µM) on fatty acid storage in (A) NHSCs and (B) THSCs at 48 h. * P<0.05; *** P<0.001 as compared with the control group.

The result (FIG. 12) showed that the *Spiranthes sinensis* extract increased the lipid accumulation in NHSCs (1.8 fold) and THSCs (1.4 fold) when compared with the control group. The observation was consistent with the results of the aforesaid Oil red O staining assay and further verified the capability of the present *Spiranthes sinensis* extract in lipid accumulation.

Example 10: The Effect of the Present *Spiranthes sinensis* Extract in Collagen Accumulation In this example, a Sirius Red stain was used for examining the effect of the present *Spiranthes sinensis* extract in Collagen accumulation. Briefly, $3\times10^4$ of cells per well were seeded in 12-well plates and were incubated in 5% $CO_2$ at 37° C. overnight for confluence. Afterward, cells were treated with various concentrations (5, 20, and 50 µg/mL) of the present *Spiranthes sinensis* extract for 24 h, respectively. Cells were washed twice with PBS, and then fixed by 3.7% paraformaldehyde (pre-warmed) for 10 min. Picro-Sirius Red solution (ScyTek, Logan, Utah, USA) was stained at RT under the dark for 1 h. Cells were washed twice with $ddH_2O$ and counterstained with Hematoxylin (Sigma-Aldrich) for 1 min. Cells were washed with distilled water for three times and stored using glycerol. Images were acquired using ZEISS inverted microscope connected with Canon 700 D camera.

Figure 13:
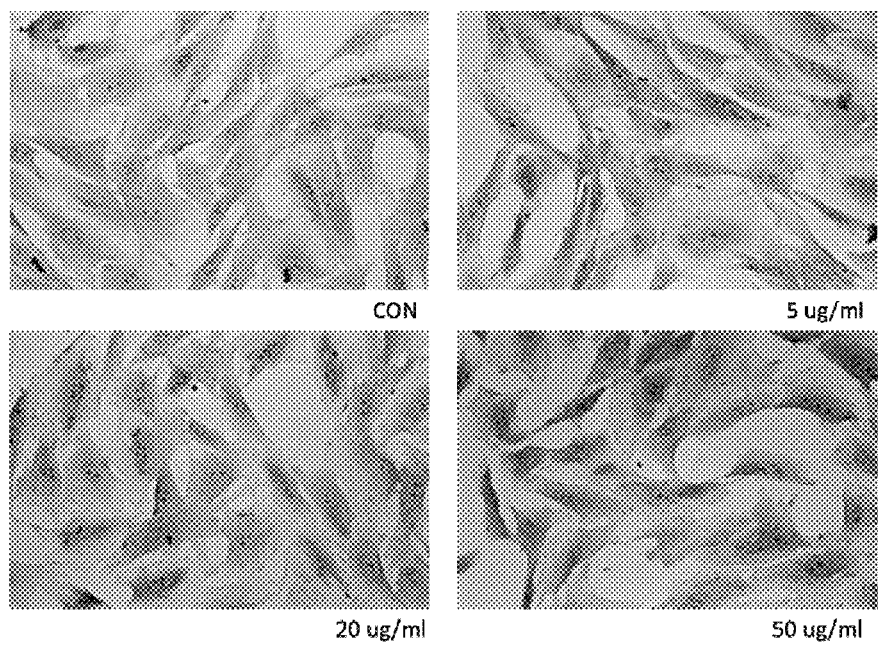
FIG. 13 shows the results of the Sirius Red stain in Example 10 under 240× magnification; wherein (A) NHSCs, untreated, or treated with 5, 20, and 50 µg/mL of *Spiranthes sinensis* extract; (B) THSCs, untreated, or treated with 5, 20, and 50 µg/mL of *Spiranthes sinensis* extract. The concentration is based on the volume of the culture medium.
Figure 13:
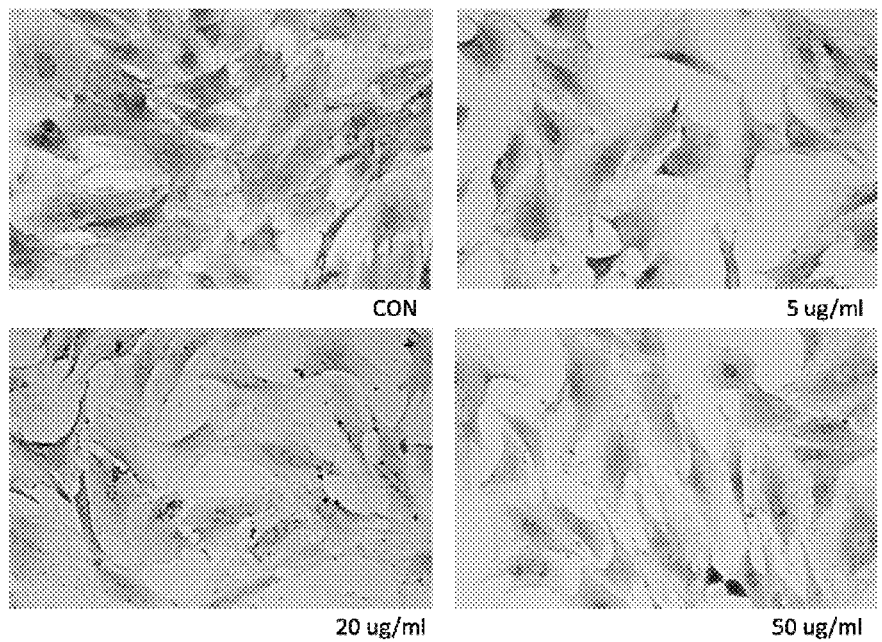

The results are shown in FIG. 13. Both NHSCs and THSCs treated with the present *Spiranthes sinensis* extract (5, 20, and 50 µg/mL) of for 24 h show reduced perinuclear collagen comparing with the control groups.

Example 11: The Effect of the Present *Spiranthes sinensis* Extract on the Activity of MMP 2

MMPs, a serials protein enzyme of biodegradable ECM, play an important role in normal or diseased cells. Liver fibrosis is a wound healing response, in which the damaged regions are refilled by ECM. Fibrosis reflects a balance between matrix production and degradation, though the degradation of ECM is a key determining factor event in hepatic fibrosis. MMPs contribute to the regression of liver fibrosis through the cleavage of fibrillar ECM and promotion of apoptosis among the activated HSCs. Hence, MMPs play dual roles of both bad and good in liver fibrosis depending on the timing.

The present *Spiranthes sinensis* extract has shown an inhibitory effect on the activity of MMP 9 (See Example 7). In this example, the activity of MMP 2 was also determined by gelatin zymography. $2\times10^5$ of HSCs were seeded into 6-well plates, after 70 to 80% confluence; cells were starved in DMEM containing 0.1% BSA for 6 h, and then treated with different concentrations (5, 20, 50, and 100 µg/mL) of the present *Spiranthes sinensis* extract for 24 h, respectively. The conditioned medium was collected, centrifuged at 12,000×g at 4° C. for 30 min to remove the cell debris. The supernatant was collected and quantified using Bradford dye (Bio-Rad). 8% SDS-PAGE gels were prepared containing 10% gelatin. Proteins were pre-heated at 55° C. with 2× loaded dye (0.125 M Tris-HCl, pH 6.8, 4% SDS, 0.04% Bromophenol blue, 20% Glycerol). 7.5 µg of protein sample was loaded into gel and electrophoresis separation was performed at 80V for 2-3 h. After electrophoresis, gel was washed 2 times in 50 mL of 2.5% Triton X-100 per gel, and then incubated in developing buffer (0.05 M Tris-HCl, pH 8.8, 5 mM $CaCl_2$, 0.02% $NaN_3$) at 37° C. for 16 h. Finally, gel was stained in 0.1% Coomassie blue R-250 (Bio-Rad) for 4 h and then destained by fixing buffer (45% methanol, 10% acetic acid). Gels were scanned using Epson scanner and quantified using multi-gauge software (Fujifilm).

Figure 14:
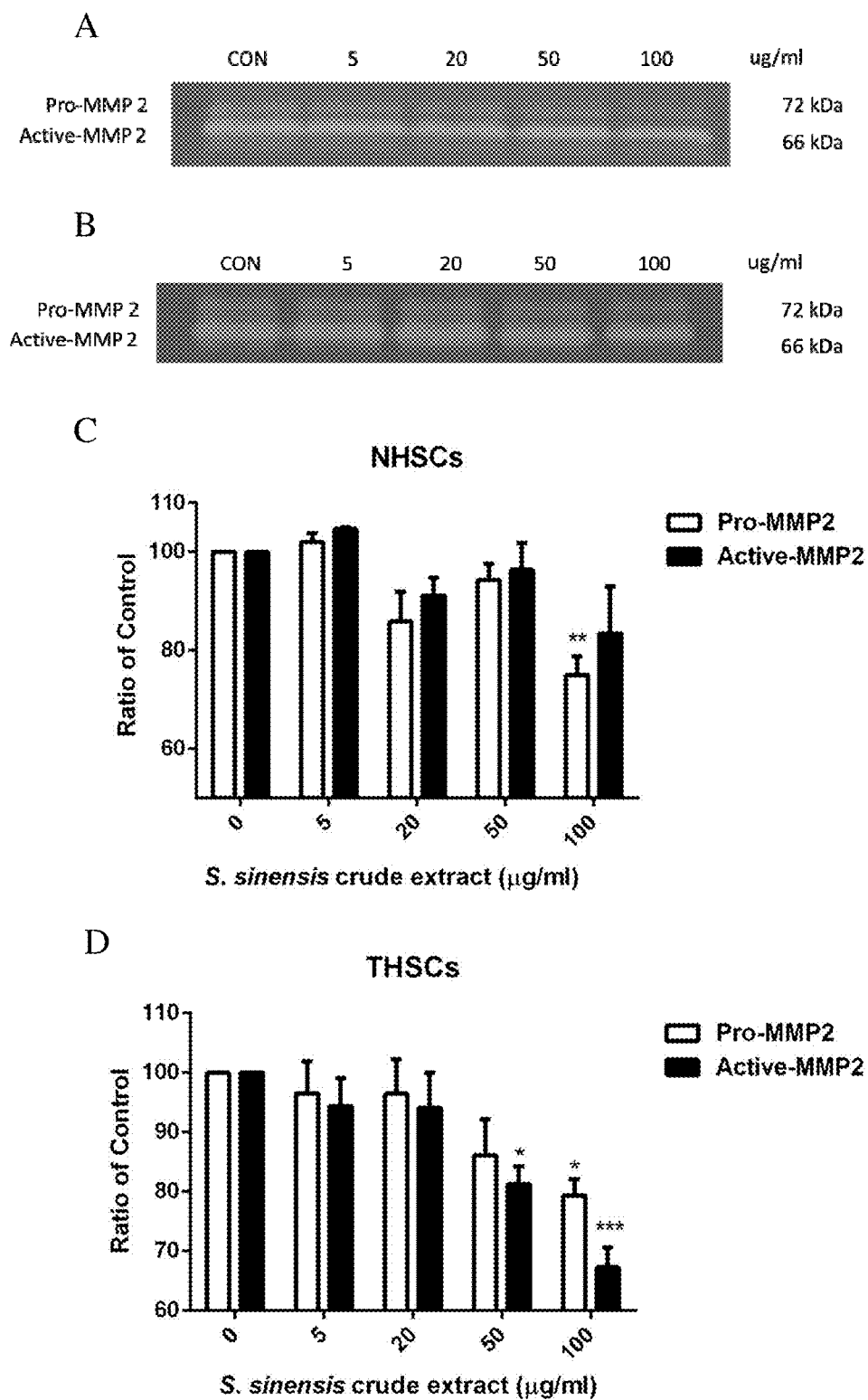
FIG. 14 shows the activity of MMP 2 examined by gelatin zymography. (A) NHSCs; (B) THSCs; (C) Quantitation from the results of (A); (D) Quantitation from the results of (B).

The results were shown in FIG. 14; wherein the activity of MMP-2 was quantified by densitometer. The MMP-2 activity was reduced in both NHSCs and THSCs treated with 5, 20, 50, and 100 μg/mL of the present *Spiranthes sinensis* extract, respectively.

Example 12: The Effect of the Present *Spiranthes sinensis* Extract on the Expression of COL1 I, COL1 III, TGF-β R1, TGF-β R2, RXRα, NrF2 and PPARγ

The expressions of COL1 III (collagen alpha 1 type III), COL1 I (collagen alpha 1 type I), TGF-β R1 (TGF-β Receptor 1), TGF-β R2 (TGF-β Receptor 2), RXRα (retinoid X receptor), NrF2 (Nuclear factor (erythroid-derived 2)-like 2) and PPARγ (peroxisome proliferator-activated receptor γ) were examined by Real-time PCR; wherein 18S was used as a control.

For RNA isolation and cDNA synthesis, $4 \times 10^5$ of HSCs were seeded into 6-well plates, after 70 to 80% confluence, and then treated with different concentrations (5, 20, 50, and 100 μg/mL) of the present *Spiranthes sinensis* extract in DMEM containing 5% FBS for 8 and 12 h, respectively. The positive control group was treated with 25 μM of curcumin. Total RNA was prepared from freshly harvested HSCs and was isolated using Trizol extraction. RNA samples were frozen at −80° C. until analyzed. cDNA was then made using an M-MLV RT kit (Invitrogen, Carlsbad, Calif.) according to the manufacturer's protocol.

For Real-time PCR, the SensiFAST SYBR No-ROX Kit (BIOLINE, London, UK) was used. PCR cycling conditions for RXRα, NrF2 and PPARγ included a 95° C. heating step for 2 min at the beginning of every run. The tubes were then cycled at 95° C. for 5 sec, annealed at 64° C. for 10 sec, and extended at 72° C. for 20 sec for forty cycles. PCR conditions for collagen alpha 1 type III, collagen alpha 1 type I, TGF-β Receptor 1, and TGF-β Receptor 2 included a 95° C. heating step for 2 min at the beginning of every run. The tubes were then cycled at 95° C. for 5 sec, annealed at 62° C. for 10 sec, and extended at 72° C. for 20 sec for 45 cycles. In all cases, optical data were collected during the annealing phase. In order to quantify expression represented by each of the PCR products, an internal reference by 18S. The primer sets used in this example were listed in the following table 2.

TABLE 2 primer sets for real-time PCR

| Name of the primer | Sequences 5'->3' | SEQ ID NO |
|---|---|---|
| 18S Forward | ACG GAC CAG AGC GAA AGC AT | SEQ ID NO 11 |
| 18S Reverse | TGT CAA TCC TGT CCG TGT CC | SEQ ID NO 12 |
| PPARγ Forward | AGC ATG GTG CCT TCG CTG ATG C | SEQ ID NO 13 |
| PPARγ Reverse | AAG TTG GTG GGC CAG AAT GGC A | SEQ ID NO 14 |
| Collagen alpha 1 type III Forward | GAA AAA ACC CTG CTC GGA ATT | SEQ ID NO 15 |
| Collagen alpha 1 type III Reverse | GGA TCA ACC CAG TAT TCT CCA CTC T | SEQ ID NO 16 |
| TGF-β Receptor 1 Forward | CAT CGG CAA AGG TCG GTT T | SEQ ID NO 17 |
| TGF-β Receptor 1 Reverse | AAT ATC TTC ACG GCA ACT TCT TCT C | SEQ ID NO 18 |
| TGF-β Receptor 2 Forward | TCA CCT ACC ACG GCT TCA CTC T | SEQ ID NO 19 |
| TGF-β Receptor 2 Reverse | CGC CCT TTT CTT TTC CTT CA | SEQ ID NO 20 |
| RXRα Forward | GCC GGC CTC TGA CTG TGA | SEQ ID NO 21 |
| RXRα Reverse | GCA CCA CAA TGT CCC AGT GA | SEQ ID NO 22 |
| NrF2 Forward | GAC AAA CAT TCA AGC CGA TTA GAG G | SEQ ID NO 23 |
| NrF2 Reverse | ACT TTA TTC TTC CCT CTC CTG CGT | SEQ ID NO 24 |

Figure 15:
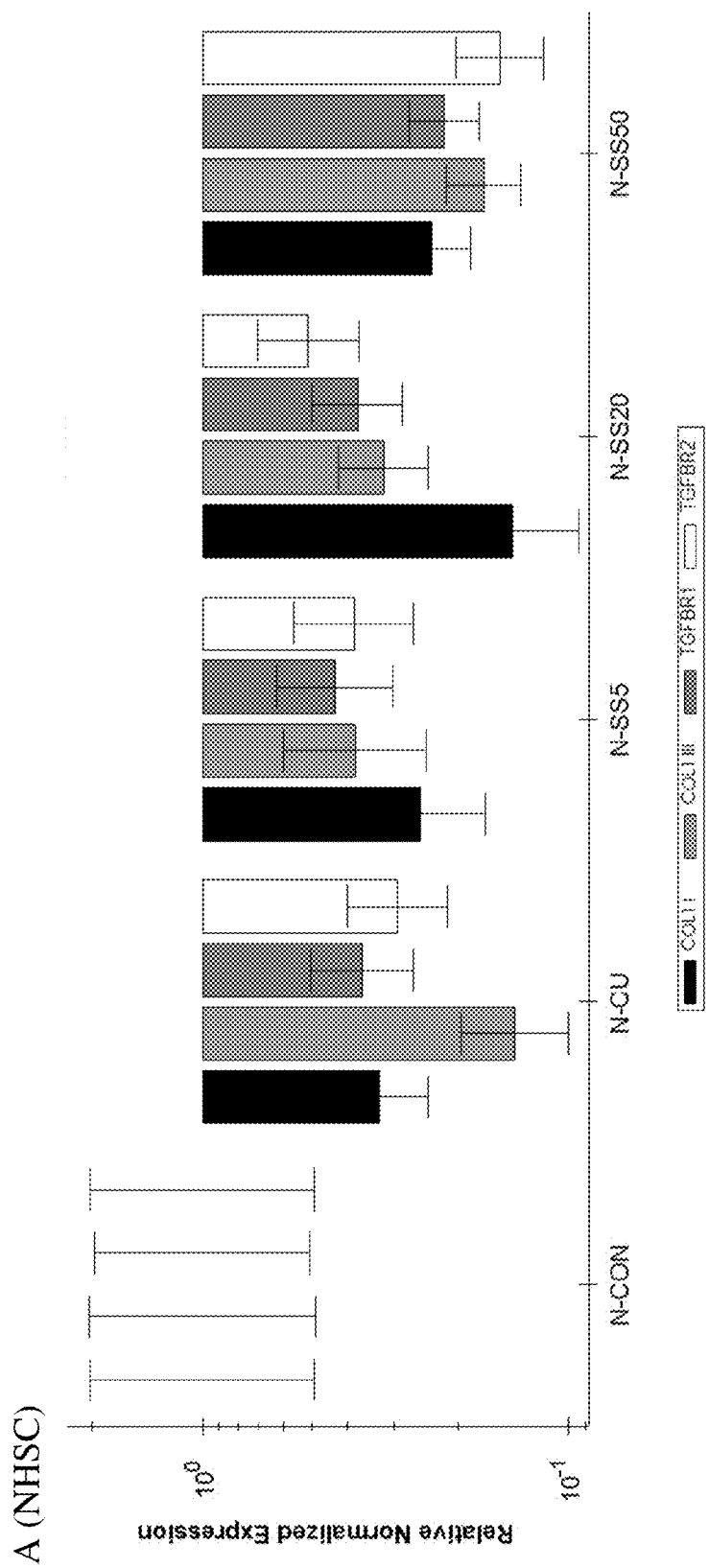
FIG. 15 shows the expression of COL1 I, COL1 III, TGF-β R1, and TGF-β R2 in both (A) NHSCs and (B) THSCs; wherein 18S is a reference gene in this examination. N-CU25: NHSCs treated with 25 µM of curcumin; N-CON: untreated NHSCs; N-SS5: NHSCs treated with 5 µg/mL of *Spiranthes sinensis* extract; N-SS20: NHSCs treated with 20 µg/mL of *Spiranthes sinensis* extract; N-SS50: NHSCs treated with 50 µg/mL of *Spiranthes sinensis* extract. T-CU25: THSCs treated with 25 µM of curcumin; T-CON: untreated THSCs; T-SS5: THSCs treated with 5 µg/mL of *Spiranthes sinensis* extract; T-SS20: THSCs treated with 20 µg/mL of *Spiranthes sinensis* extract; T-SS50: THSCs treated with 50 µg/mL of *Spiranthes sinensis* extract. The concentration is based on the volume of the culture medium. Data represent the mean±SEM from three separate experiments.

FIG. 15 showed that NHSCs and THSCs treated with the present *Spiranthes sinensis* extract for 8 h had reduced expression of COL1 I, COL1 III, TGFBR1, and TGFBR2.

Figure 16:
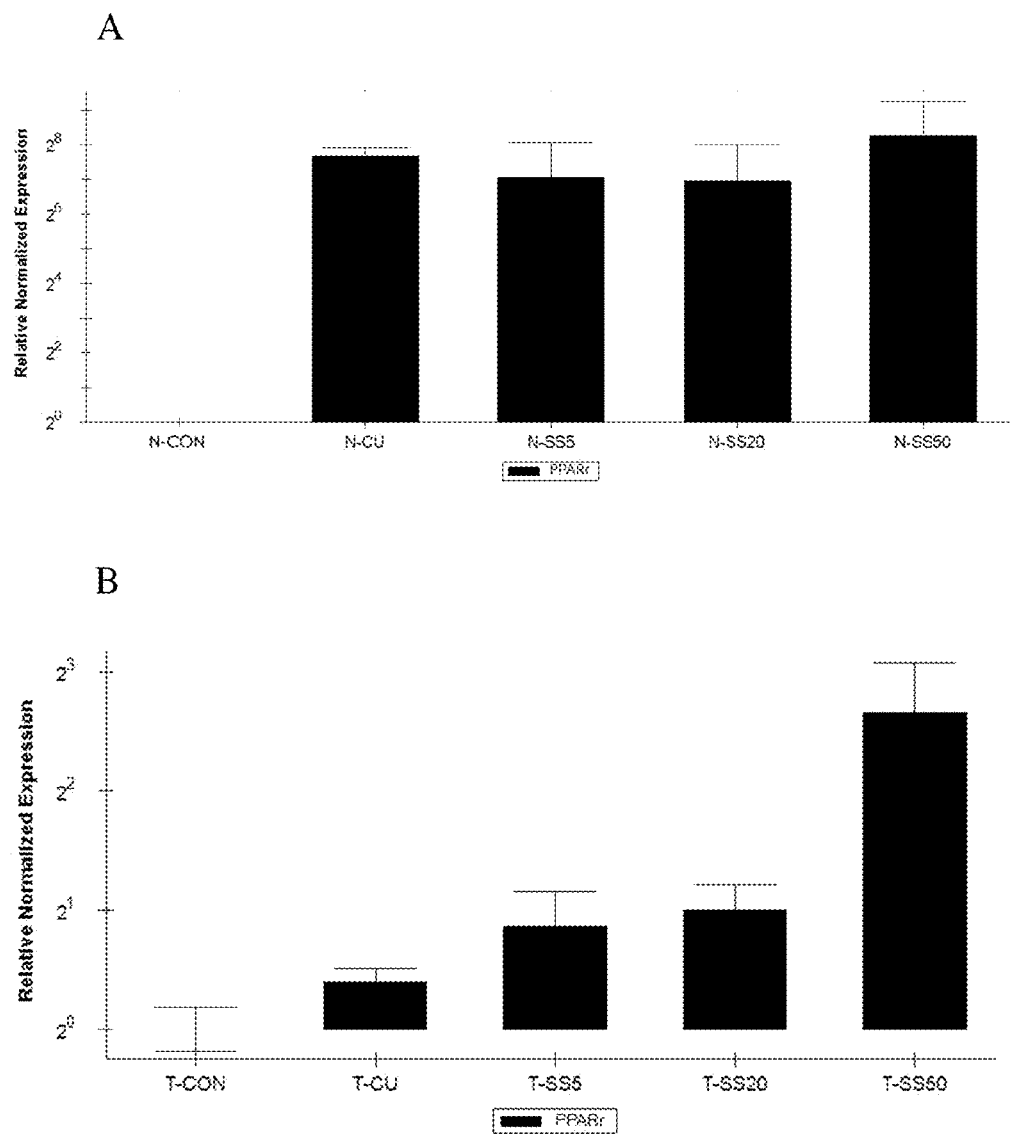
FIG. 16 shows the expression of PPARγ in both NHSCs and THSCs. N-Control: untreated NHSCs; N-SS5: NHSCs treated with 5 µg/mL of *Spiranthes sinensis* extract; N-SS20: NHSCs treated with 20 µg/mL of *Spiranthes sinensis* extract; N-SS50: NHSCs treated with 50 µg/mL of *Spiranthes sinensis* extract. N-CU25: NHSCs treated with 25 µM of curcumin. T-Control: untreated THSCs; T-SS5: THSCs treated with 5 µg/mL of *Spiranthes sinensis* extract; T-SS20: THSCs treated with 20 µg/mL of *Spiranthes sinensis* extract; T-SS50: THSCs treated with 50 µg/mL of *Spiranthes sinensis* extract. THSCs treated with 25 µM of curcumin. The gene expression was normalized by the expression of 18S. The concentration is based on the volume of the culture medium. Data represent the mean±SEM from three separate experiments.
Figure 17:
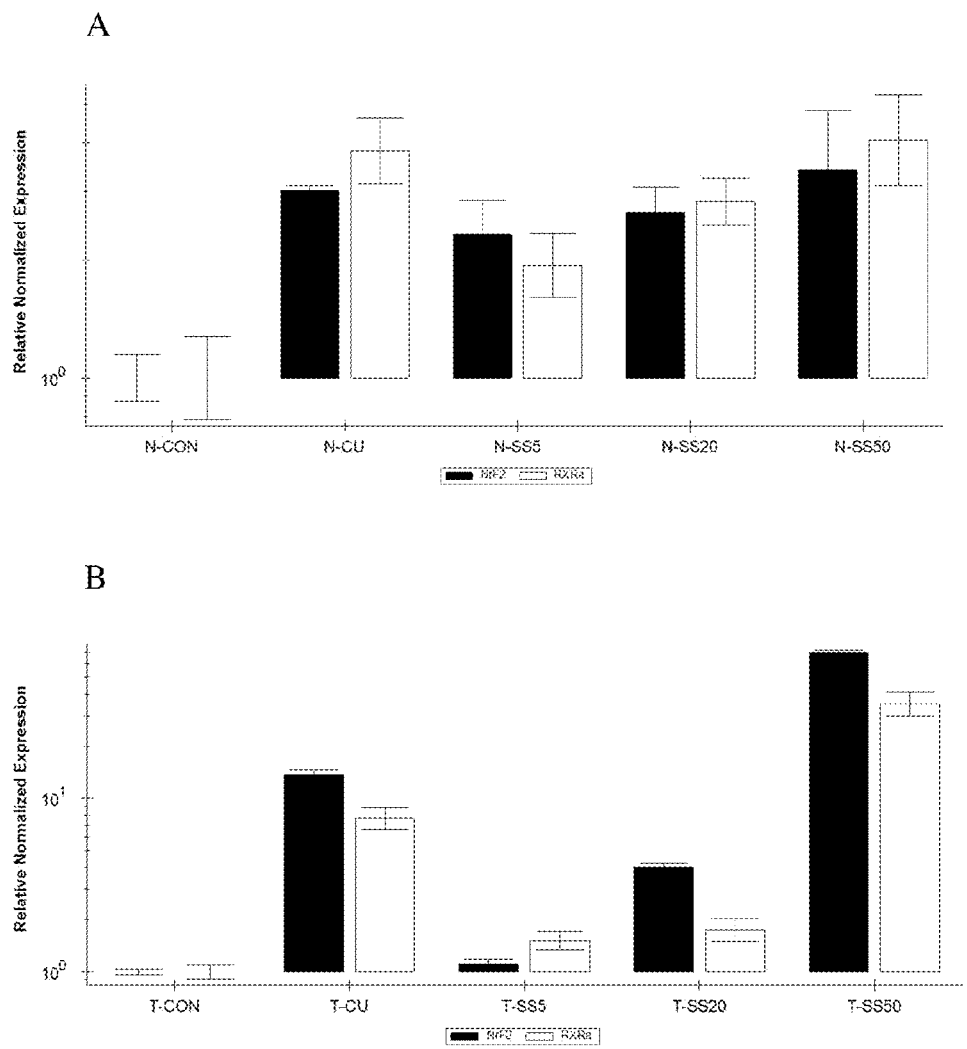
FIG. 17 shows the expression of RXRα, NrF2 in both NHSCs and THSCs. N-Control: untreated NHSCs; N-SS5: NHSCs treated with 5 µg/mL of *Spiranthes sinensis* extract; N-SS20: NHSCs treated with 20 µg/mL of *Spiranthes sinensis* extract; N-SS50: NHSCs treated with 50 µg/mL of *Spiranthes sinensis* extract. N-CU25: NHSCs treated with 25 µM of curcumin. T-Control: untreated THSCs; T-SS5: THSCs treated with 5 µg/mL of *Spiranthes sinensis* extract; T-SS20: THSCs treated with 20 µg/mL of *Spiranthes sinensis* extract; T-SS50: THSCs treated with 50 µg/mL of *Spiranthes sinensis* extract. THSCs treated with 25 µM of curcumin. The gene expression was normalized by the expression of 18S. The concentration is based on the volume of the culture medium. Data represent the mean±SEM from three separate experiments.

FIGS. 16 and 17 showed that RXRα, NrF2 and PPARγ gene expression increased in both NHSCs and THSCs treated with the present *Spiranthes sinensis* extract for 12 h treatment.

REFERENCES

1. Uetake, Y. & Peterson, R. L. Changes in actin filament arrays in protocorm cells of the orchid species, *Spiranthes sinensis*, induced by the symbiotic fungus Ceratobasidium cornigerum. *Can J Bot* 75, 1661-1669 (1997).
2. Sun, M. Effects of population size, mating system, and evolutionary origin on genetic diversity in *Spiranthes sinensis* and S-hongkongensis. *Conserv Biol* 10, 785-795 (1996).

3. Lin, Y. L., Huang, R. L., Don, M. J. & Kuo, Y. H. Dihydrophenanthrenes from *Spiranthes sinensis*. *J Nat Prod* 63, 1608-1610 (2000).
4. Lin, Y. L., Wang, W. Y., Kuo, Y. H. & Liu, Y. H. Homocyclotirucallane and two dihydrophenanthrenes from *Spiranthes sinensis*. *Chem Pharm Bull* 49, 1098-1101 (2001).
5. Li, C. Y., et al. New dimeric phenanthrene and flavone from *Spiranthes sinensis*. *J Asian Nat Prod Res* 15, 417-421 (2013).
6. Peng, J. Y., et al. Two new prenylated coumarins from *Spiranthes sinensis* (Pers.) Ames. *J Asian Nat Prod Res* 10, 279-283 (2008).
7. Nakerakanti, S. & Trojanowska, M. The Role of TGF-beta Receptors in Fibrosis. *The open rheumatology journal* 6, 156-162 (2012).
8. Fu, Y., Zheng, S., Lin, J., Ryerse, J. & Chen, A. Curcumin protects the rat liver from CC14-caused injury and fibrogenesis by attenuating oxidative stress and suppressing inflammation. *Molecular pharmacology* 73, 399-409 (2008).
9. Zheng, S. & Chen, A. Activation of PPARgamma is required for curcumin to induce apoptosis and to inhibit the expression of extracellular matrix genes in hepatic stellate cells in vitro. *The Biochemical journal* 384, 149-157 (2004).

What is claimed is:

1. A method for treating inflammation in a subject in need thereof comprising administering an effective amount of an ethyl acetate extract of *Spiranthes sinensis* to said subject, wherein said effective amount is 0.6 to 5 mg/60 kg body weight/day, and wherein said ethyl acetate extract of *Spiranthes sinensis* is obtained by:

i.) obtaining a *Spiranthes sinensis* plant;

ii.) mixing said *Spiranthes sinensis* plant with ethyl acetate to obtain a mixture, wherein ethyl acetate is the only solvent used; and iii.) drying said mixture to obtain the ethyl extract of *Spiranthes sinensis*.

2. The method of claim 1, wherein said administrating is via oral administration, intravenous injection, or a combination thereof.

3. The method of claim 1, wherein said *Spiranthes sinensis* extract is administrated with a pharmaceutically acceptable carrier; selected from the group consisting of water, alcohol, glycerol, chitosan, alginate, chondroitin, Vitamin E, mineral oil, dimethyl sulfoxide (DMSO), or a combination thereof.

4. The method of claim 1, wherein said plant is dried and/or ground before mixing with said solvent.

5. The method of claim 1, wherein said mixing is conducted at 20 to 28° C.

6. The method of claim 1, wherein said mixing is conducted for 1 to 2 days.

7. The method of claim 1, wherein said drying is achieved by vacuum drying.

8. A method for treating inflammation in a subject in need thereof comprising:
   a.) preparing an ethyl acetate extract of *Spiranthes sinensis* by:
      i.) obtaining a *Spiranthes sinensis* plant;
      ii.) mixing said *Spiranthes sinensis* plant with ethyl acetate to obtain a mixture, wherein said ethyl acetate is the only solvent used; and
      iii.) drying said mixture to obtain said extract; and
   b.) administering 0.6 to 5 mg/60 kg body weight/day of the ethyl acetate extract of *Spiranthes sinensis* to the subject.

* * * * *

SEQUENCE LISTING

```
<160> NUMBER OF SEQ ID NOS: 24

<210> SEQ ID NO 1
<211> LENGTH: 22
<212> TYPE: DNA
<213> ORGANISM: Artificial Sequence
<220> FEATURE:
<223> OTHER INFORMATION: primer

<400> SEQUENCE: 1
agtggtacga ccagaggcat ac                                              22

<210> SEQ ID NO 2
<211> LENGTH: 22
<212> TYPE: DNA
<213> ORGANISM: Artificial Sequence
<220> FEATURE:
<223> OTHER INFORMATION: primer

<400> SEQUENCE: 2
atgggtcaga aggactccta cg                                              22

<210> SEQ ID NO 3
<211> LENGTH: 18
<212> TYPE: DNA
<213> ORGANISM: Artificial Sequence
<220> FEATURE:
<223> OTHER INFORMATION: primer

<400> SEQUENCE: 3
tcctacacca caccaaac                                                   18

<210> SEQ ID NO 4
<211> LENGTH: 19
<212> TYPE: DNA
<213> ORGANISM: Artificial Sequence
<220> FEATURE:
<223> OTHER INFORMATION: primer

<400> SEQUENCE: 4
ctccaatctc tgcctatcc                                                  19

<210> SEQ ID NO 5
<211> LENGTH: 18
<212> TYPE: DNA
<213> ORGANISM: Artificial Sequence
<220> FEATURE:
<223> OTHER INFORMATION: primer

<400> SEQUENCE: 5
aaccctctgg cccaagga                                                   18
```

-continued

```
<210> SEQ ID NO 6
<211> LENGTH: 18
<212> TYPE: DNA
<213> ORGANISM: Artificial Sequence
<220> FEATURE:
<223> OTHER INFORMATION: primer

<400> SEQUENCE: 6
ggcgacgggc ttatctga                                                  18

<210> SEQ ID NO 7
<211> LENGTH: 21
<212> TYPE: DNA
<213> ORGANISM: Artificial Sequence
<220> FEATURE:
<223> OTHER INFORMATION: primer

<400> SEQUENCE: 7
atgaactccc tctccacaag c                                              21

<210> SEQ ID NO 8
<211> LENGTH: 21
<212> TYPE: DNA
<213> ORGANISM: Artificial Sequence
<220> FEATURE:
<223> OTHER INFORMATION: primer

<400> SEQUENCE: 8
tggctttgtc tggattctttc                                               21

<210> SEQ ID NO 9
<211> LENGTH: 19
<212> TYPE: DNA
<213> ORGANISM: Artificial Sequence
<220> FEATURE:
<223> OTHER INFORMATION: primer

<400> SEQUENCE: 9 aaagggact tgaagagag                                                  19

<210> SEQ ID NO 10
<211> LENGTH: 21
<212> TYPE: DNA
<213> ORGANISM: Artificial Sequence
<220> FEATURE:
<223> OTHER INFORMATION: primer

<400> SEQUENCE: 10
ctgcttgaga ggtgctgatg t                                              21

<210> SEQ ID NO 11
<211> LENGTH: 20
<212> TYPE: DNA
<213> ORGANISM: Artificial Sequence
<220> FEATURE:
<223> OTHER INFORMATION: primer

<400> SEQUENCE: 11
acggaccaga gcgaaagcat                                                20

<210> SEQ ID NO 12
<211> LENGTH: 20
<212> TYPE: DNA
<213> ORGANISM: Artificial Sequence
<220> FEATURE:
<223> OTHER INFORMATION: primer
```

<400> SEQUENCE: 12
tgtcaatcct gtccgtgtcc                                                       20

<210> SEQ ID NO 13
<211> LENGTH: 22
<212> TYPE: DNA
<213> ORGANISM: Artificial Sequence
<220> FEATURE:
<223> OTHER INFORMATION: primer

<400> SEQUENCE: 13
agcatggtgc cttcgctgat gc                                                    22

<210> SEQ ID NO 14
<211> LENGTH: 22
<212> TYPE: DNA
<213> ORGANISM: Artificial Sequence
<220> FEATURE:
<223> OTHER INFORMATION: primer

<400> SEQUENCE: 14
aagttggtgg gccagaatgg ca                                                    22

<210> SEQ ID NO 15
<211> LENGTH: 21
<212> TYPE: DNA
<213> ORGANISM: Artificial Sequence
<220> FEATURE:
<223> OTHER INFORMATION: primer

<400> SEQUENCE: 15
gaaaaaaccc tgctcggaat t                                                     21

<210> SEQ ID NO 16
<211> LENGTH: 25
<212> TYPE: DNA
<213> ORGANISM: Artificial Sequence
<220> FEATURE:
<223> OTHER INFORMATION: primer

<400> SEQUENCE: 16
ggatcaaccc agtattctcc actct                                                 25

<210> SEQ ID NO 17
<211> LENGTH: 19
<212> TYPE: DNA
<213> ORGANISM: Artificial Sequence
<220> FEATURE:
<223> OTHER INFORMATION: primer

<400> SEQUENCE: 17
catcggcaaa ggtcggttt                                                        19

<210> SEQ ID NO 18
<211> LENGTH: 25
<212> TYPE: DNA
<213> ORGANISM: Artificial Sequence
<220> FEATURE:
<223> OTHER INFORMATION: primer

<400> SEQUENCE: 18
aatatcttca cggcaacttc ttctc                                                 25

<210> SEQ ID NO 19

```
<211> LENGTH: 22
<212> TYPE: DNA
<213> ORGANISM: Artificial Sequence
<220> FEATURE:
<223> OTHER INFORMATION: primer

<400> SEQUENCE: 19
tcacctacca cggcttcact ct                                            22

<210> SEQ ID NO 20
<211> LENGTH: 20
<212> TYPE: DNA
<213> ORGANISM: Artificial Sequence
<220> FEATURE:
<223> OTHER INFORMATION: primer

<400> SEQUENCE: 20
cgcccttttc ttttccttca                                               20

<210> SEQ ID NO 21
<211> LENGTH: 18
<212> TYPE: DNA
<213> ORGANISM: Artificial Sequence
<220> FEATURE:
<223> OTHER INFORMATION: primer

<400> SEQUENCE: 21
gccggcctct gactgtga                                                 18

<210> SEQ ID NO 22
<211> LENGTH: 20
<212> TYPE: DNA
<213> ORGANISM: Artificial Sequence
<220> FEATURE:
<223> OTHER INFORMATION: primer

<400> SEQUENCE: 22
gcaccacaat gtcccagtga                                               20

<210> SEQ ID NO 23
<211> LENGTH: 25
<212> TYPE: DNA
<213> ORGANISM: Artificial Sequence
<220> FEATURE:
<223> OTHER INFORMATION: primer

<400> SEQUENCE: 23
gacaaacatt caagccgatt agagg                                         25

<210> SEQ ID NO 24
<211> LENGTH: 24
<212> TYPE: DNA
<213> ORGANISM: Artificial Sequence
<220> FEATURE:
<223> OTHER INFORMATION: primer

<400> SEQUENCE: 24
actttattct tccctctcct gcgt                                          24
```